(12) United States Patent
Schumacher et al.

(10) Patent No.: US 7,922,731 B2
(45) Date of Patent: Apr. 12, 2011

(54) SURGICAL INSTRUMENT AND OSTEOSYNTHESIS DEVICE

(75) Inventors: Joerg Schumacher, Tuttlingen (DE); Brian E. Dalton, Erie, PA (US); Ulrich Hahn, Rheinberg (DE)

(73) Assignee: Aesculap AG, Tuttlingen (DE)

( * ) Notice: Subject to any disclaimer, the term of this patent is extended or adjusted under 35 U.S.C. 154(b) by 937 days.

(21) Appl. No.: 11/644,725

(22) Filed: Dec. 22, 2006

(65) Prior Publication Data

US 2008/0154280 A1 Jun. 26, 2008

(51) Int. Cl.
*A61B 17/58* (2006.01)
*A61B 17/60* (2006.01)
*A61F 2/00* (2006.01)

(52) U.S. Cl. .............................. 606/104; 606/96; 606/99

(58) Field of Classification Search .................. 606/104, 606/246, 300, 86 A, 99, 146, 304, 96; 81/52, 81/467, 473–478, 784, 445–450

See application file for complete search history.

(56) References Cited

U.S. PATENT DOCUMENTS

| | | | |
|---|---|---|---|
| 6,530,929 | B1 | 3/2003 | Justis et al. |
| 6,929,606 | B2 | 8/2005 | Ritland |
| 6,964,665 | B2 | 11/2005 | Thomas et al. |
| 7,008,422 | B2 | 3/2006 | Foley et al. |
| 2004/0158260 | A1 | 8/2004 | Blau et al. |
| 2004/0215190 | A1 | 10/2004 | Nguyen et al. |
| 2005/0131422 | A1 | 6/2005 | Anderson et al. |
| 2005/0154389 | A1 | 7/2005 | Selover et al. |
| 2005/0159757 | A1 | 7/2005 | Shluzas et al. |
| 2005/0192589 | A1 | 9/2005 | Raymond et al. |
| 2005/0228400 | A1 | 10/2005 | Chao et al. |
| 2005/0245928 | A1 | 11/2005 | Colleran et al. |
| 2008/0125788 | A1* | 5/2008 | Cohen et al. ................... 606/104 |
| 2008/0177274 | A1* | 7/2008 | Gil et al. ......................... 606/99 |

FOREIGN PATENT DOCUMENTS

| | | |
|---|---|---|
| EP | 1 413 257 B1 | 4/2004 |
| EP | 1 523 950 A1 | 4/2005 |
| WO | WO 2004/004549 A2 | 1/2004 |
| WO | WO 2005/018490 A2 | 3/2005 |
| WO | WO 2005/037065 A2 | 4/2005 |
| WO | WO 2005/041799 A1 | 5/2005 |
| WO | WO 2005/058386 A1 | 6/2005 |
| WO | WO 2005/092218 A1 | 10/2005 |
| WO | WO 2006/029373 A1 | 3/2006 |
| WO | WO 2006/052504 A2 | 5/2006 |

* cited by examiner

*Primary Examiner* — Eduardo C Robert
*Assistant Examiner* — Christina Negrelli
(74) *Attorney, Agent, or Firm* — RatnerPrestia

(57) ABSTRACT

A surgical instrument for applying and fixing a fixation screw to a threaded section of a head of a bone anchorage element comprises a distal end and a proximal end, a first tool member and a second tool member. The first tool member is arranged at the distal end and adapted for engaging the threaded section of the bone anchorage element head. The second tool member is adapted for engaging a tool-engaging member of the fixation screw. The instrument is constructed such that in a working position of the instrument the second tool member is supported on the instrument in a torque proof manner relative to the first tool member about a longitudinal axis and is movable parallel to the longitudinal axis relative to the first tool member. Moreover, an osteosynthesis device comprising at least two bone anchorage elements and at least one connection member is suggested. Further, a method for fixing an osteosynthesis device on two vertebrae of a spinal column in a minimal invasive manner is proposed.

50 Claims, 13 Drawing Sheets

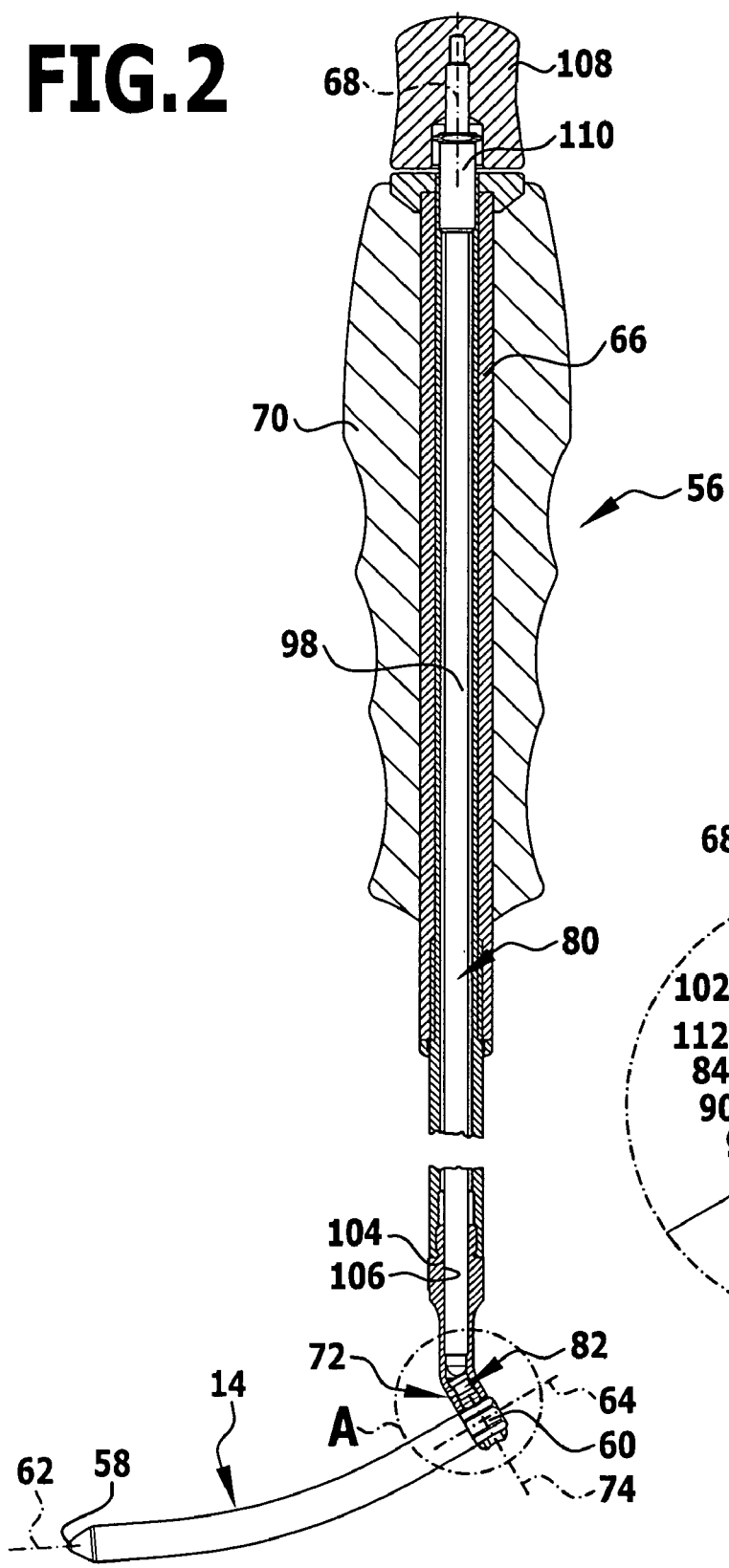
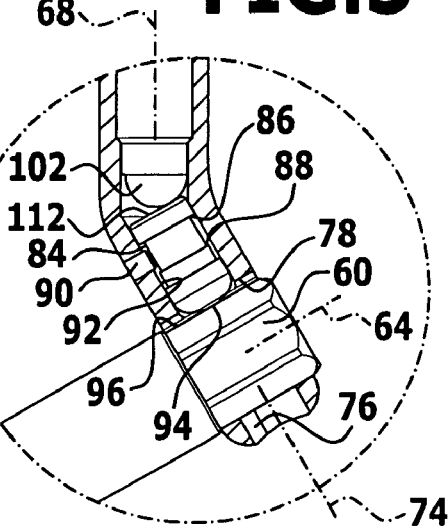

SURGICAL INSTRUMENT AND OSTEOSYNTHESIS DEVICE

FIELD OF THE INVENTION

The present invention relates to a surgical instrument for applying and fixing a fixation screw to a threaded section of a head of a bone anchorage element.

Furthermore, the present invention relates to an osteosynthesis device comprising at least two bone anchorage elements and at least one connection member, at least one of the at least two bone anchorage elements comprising a U-shaped receptacle for receiving at least a part of the at least one connection member, the at least one bone screw comprising a fixation screw for securing the at least one connection member in the receptacle in a connection position.

Moreover, the present invention relates to a method for fixing an osteosynthesis device on two vertebrae of a spinal column in a minimal invasive manner.

BACKGROUND OF THE INVENTION

Osteosynthesis devices of the type described hereinabove are used for stabilization of the spinal column of a human or animal body, in particular, if a vertebra or an intervertebral disk is damaged. For this purpose bone anchoring elements, for example, bone screws, are fixed on the vertebrae which are to be linked with the osteosynthesis device. In a next step a connection member, for instance, a rod, is inserted into the retainers or receptacles provided on the bone anchorage elements for receiving the connection member. After insertion of the connection member in the retainers of both anchorage elements, the connection member has to be fixed on the bone anchorage elements. It is known to use fixation screws for this purpose which can be screwed into threaded sections, for example, of heads of the bone anchorage elements. Inserting and tightening the fixation screws on the bone anchorage elements is difficult, even if the patient's body is widely opened for implanting the osteosynthesis device.

Obviously introducing such a fixation screw into the patient's body, inserting the fixation screw into the threaded section of the bone anchorage element and tightening the same in order to fix the connection member to the bone anchorage element are difficult and require enhanced skills on the part of the surgeon, in particular, if this procedure is to be carried out using a minimal invasive access to the patient's body.

The object underlying the invention is, therefore, to provide an improved surgical instrument and an osteosynthesis device of the type described hereinabove, which allow facilitated implanting of the device using a minimal invasive access to the patient's body. Moreover, it would be simpler and easier if a method were available for fixing the osteosynthesis device onto vertebrae of a spinal column in a minimal invasive manner.

SUMMARY OF THE INVENTION

In accordance with the invention it is advantageous to provide a surgical instrument of the type described hereinabove wherein the instrument comprises a distal end and a proximal end, a first tool member and a second tool member, the first tool member being arranged at the distal end and adapted for engaging the threaded section of the bone anchorage element head, and the second tool member being adapted for engaging a tool-engaging member of the fixation screw, wherein in a working position of the instrument, the second tool member is supported on the instrument in a torque proof manner relative to the first tool member about a longitudinal axis and is movable parallel to the longitudinal axis relative to the first tool member.

With such an improved instrument it is possible to screw in the fixation screw into the threaded section of the bone anchorage element head while the instrument itself is in engagement, for example, relation with the threaded section of the bone anchorage element head. Thus, a surgeon can easily screw a fixation screw into the threaded section of the head without any problems. The movable construction of the first tool member and the second tool member relative to each other with respect to the longitudinal axis allows, in particular, the bone fixation screw and the first tool member to be screwed into the threaded section of the head at the same time. The axial movability of the tool members relative to each other allows use of any fixation screw having threads that correspond to the threaded section of the head. In particular, it is then not important where the first turn of the fixation screw threads starts on the fixation screw. Due to the axial movability both the fixation screw threads and the first tool member can engage the threaded section of the bone anchorage element head in such a way that they can be screwed in at the same time without a seizing action of the parts engaging each other.

It is expedient for the first tool member to be provided at a distal end of a first hollow shaft. Thus, the first hollow shaft can be easily connected to the bone anchorage element and can be used as a guide, for example, for the second tool member. Therefore, a surgeon no longer needs to aim with the second tool member for engaging the fixation screw but the surgeon can just use the first hollow shaft as a guide for the second tool member for engaging the tool-engaging member of the fixation screw.

In order to simplify the construction of the instrument to allow support of the second tool member on the instrument in a torque proof manner, it is advantageous for the first hollow shaft to have an internal non-circular cross section. Such a design permits, for example, turning of the shaft and turning of the second tool member with exactly the same rotational speed. This facilitates the screwing-in action of the fixation screw into the threaded section of the bone anchorage element head.

Preferably, the internal non-circular cross section is of polygonal shape. This allows the use of commonly used alien keys, in particular, alien keys having a hexagonal or octagonal cross section.

In order to further simplify the construction of the surgical instrument, it is expedient for the second tool member to be arranged at a distal end of a shank. Although it would be conceivable to provide the shank over its entire length with a cross section adapted for engaging the tool-engaging member of the fixation screw, the manufacture of the shank is easier if the second tool member is only provided on the distal end of the shank.

In order to support the second tool member on the instrument in a torque proof manner, it is advantageous for the shank to comprise a shaft-engaging portion which has a first outer non-circular cross section. Such a design enables, in cooperation with a more or less corresponding inner cross section of the shaft, support of the second tool member on the instrument in a torque proof manner relative to the shaft.

Preferably, the first outer non-circular cross section is of polygonal shape. Semi-finished products, in particular metal rods are available at low cost, and, therefore, reduce the expenditure in manufacturing. For example, the non-circular cross section can be of hexagonal or octagonal shape.

Preferably, the second tool member is arranged at a distal end of the shaft-engaging section. In particular, if the second tool member is arranged at the distal end of the shaft-engaging section makes it easier to engage the tool-engaging member of the fixation screw with the second tool member.

According to a preferred embodiment of the invention, it can be expedient for the internal cross section of the first shaft and the external cross section of the shaft-engaging section of the shank to be designed such that the shank is insertable into and movable relative to the shaft parallel to the longitudinal axis and that the shank and the shaft are supported on the instrument in a torque proof manner relative to each other. Such a design allows a rotary movement of both the shaft and the shank at the same time at the same rotational speed. Thus, it is easy to engage the threaded section of the bone anchorage element head with both the fixation of the screw and the first tool member.

The first tool member can be easily screwed in into the threaded section of the bone anchorage element head if the first tool member comprises a first externally threaded section corresponding to the internally threaded section of the bone anchorage element head.

In order to allow tightening of the fixation screw on the bone anchorage element for fixing the connection member on the bone anchorage element, it is advantageous for the second tool member to have a second outer non-circular cross section corresponding to an internal noncircular cross section of the tool-engaging member. Preferably, both cross sections correspond to each other in such a way that there is almost no play so that a torque can be transmitted from the second tool member to the fixation screw in an optimal way.

In order to allow the use of commonly available fixation screws, preferably, the second outer non-circular cross section is of polygonal shape. In particular, the second outer non-circular cross section can be of hexagonal or octagonal shape. This allows the use of, for example, alien keys for tightening the fixation screw on the bone anchorage element.

The design of the surgical instrument can be easily simplified by the first and second outer cross sections being identical. Thus, it is possible to use a shank in the form of a rod having a polygonal cross section over its entire length, for example, a rod with a hexagonal or octagonal cross section.

In accordance with a preferred embodiment of the invention, it is advantageous for a locking mechanism to be provided for locking the shaft and the shank relative to each other in at least one locking position in a direction parallel to the longitudinal axis. The at least one locking position is preferably defined in such a way that a relative movement of the shaft and the shank is still possible at least in a limited range, for example, in a range of from 1 to 5 mm. However, the at least one locking position, can, of course, also be provided in such a way that a relative axial movement of the shaft and the shank is impossible. Provision of the locking mechanism has the further advantage that the shank and the shaft cannot be disengaged from each other unintentionally.

Preferably, the locking mechanism is designed such that two locking positions are provided. This allows, for example, the shaft and the shank to be in a first locking position in a relation so that the second tool member engages the tool-engaging member of the fixation screw, and in the other locking position, the second tool member disengages from the tool-engaging member of the fixation screw. This has the further advantage that the shaft can be unscrewed from the threaded section of the bone anchorage element head without unscrewing the fixation screw.

In accordance with a preferred embodiment of the invention, it is provided that in a first locking position the second tool member extends beyond the distal end of the shaft, and in a second locking position the second tool member is retracted in proximal direction into the shaft. This makes it possible, in particular, to screw in the fixation screw and the first tool member into the threaded section of the bone anchorage element head, whereas, for disengaging the instrument from the bone anchorage element, the second tool member can be retracted so that only the first tool member can be unscrewed from the bone anchorage element head but the fixation screw remains in its tightened position.

Preferably, the locking mechanism comprises a first locking member and at least one second locking member, with the first locking member engaging the at least one second locking member in the at least one locking position, and the first locking member disengaging from the at least one second locking member in a release position. Thus, it is easy to transfer the surgical instrument from a locking position, in which the shank and the shaft are secured relative to each other, to a release position, in which the shank and the shaft can, for example, be disassembled for cleaning purposes.

The design of the surgical instrument can be further simplified by the first locking member being movably supported on the shank, and by the at least one second locking member being arranged on the shaft. Such a construction constitutes a particularly simple way of securing and releasing the shank and the shaft to and from each other.

The design of the surgical instrument can be further simplified by the at least one second locking member being designed in the form of a locking recess.

Preferably, the locking recess is designed in the form of a peripheral groove. A peripheral groove has, in particular, the advantage that it allows engagement with a corresponding locking member independent of a rotational position.

It is expedient for a first stop to be provided for defining and separating axial locking positions. Such a stop can, in particular, define not only one but both locking positions.

Preferably, the stop is designed in the form of a peripheral projection axially separating two second locking members. For example, such a stop can be easily formed by a remaining peripheral side wall separating two peripheral grooves.

In order to maintain a locking position without a person applying a constant force to the instrument, it is advantageous for the first locking member to be biased into engagement with the at least one second locking member. This means, in particular, that the first and second locking members are kept in engagement relative to each other in position which can also be called a normal position of the instrument.

It is favorable for a bias member to be provided for biasing the first locking member into engagement with the at least one second locking member. This allows choosing a bias member which is adapted for constraining the locking members into the locking position.

The construction of the instrument can be further simplified by the bias member being a spring. The spring can, in particular, be in the form of a coil spring or a leaf spring.

In accordance with a preferred embodiment of the invention, a proximal end of the shank extends beyond a proximal end of the shaft in the at least one locking position. This allows grasping of the proximal end of the shaft with a tool, or the hand of a user to apply a force or a torque to the shank for screwing the fixation screw into the threaded section of the bone anchorage element head.

To provide improved handling of the instrument by a user, in particular, a surgeon, it is expedient for a handle to be provided at the proximal end of the instrument.

Preferably, the handle is releasably connectable to the instrument. This allows simple disassembly of the instrument, in particular, for cleaning purposes. Moreover, it is thus possible for a user to choose handle for connection with the instrument individually.

In principle, it would be conceivable to provide a handle which is connectable to the shaft, in particular, to a proximal end of the shaft. However, it is advantageous for the handle to be releasably connectable to the proximal end of the shank. Such a design allows transmission of a force applied to the handle via the shank to the second tool member and directly to the fixation screw. Thus, manufacturing tolerances which can affect a connection of the shank and the shaft are of no importance.

According to a further preferred embodiment of the invention it can be advantageous for the instrument to further comprise a tubular outer sleeve which is engageable with the bone anchorage element and which is configured to receive the first and second tool members. First, such a sleeve can be used to protect the first and second tool members or surrounding tissues from contacting the first and second tool members when they are introduced into a patient's body. Secondly, the sleeve enables an improved connection between the instrument and the bone anchorage element, which, in particular, increases the stability of the system and facilitates the surgical operation.

Preferably, the sleeve is dimensioned such that the first hollow shaft is insertable into and extractable out of the sleeve in a direction parallel to a longitudinal axis defined by the sleeve. By this means the sleeve can be used also as a guide for the shaft, which simplifies engaging the bone anchorage element, in particular, with a distal end of the shaft.

Preferably, the instrument further comprises at least one distractor-engaging portion for connecting the instrument to a distractor. Distractors are usually used for moving the vertebrae which are to be connected to each other by means of the osteosynthesis device into a desired position, for example, into a distracted position. Distraction of the vertebrae is, for example, necessary if the intervertebral disc is removed, which requires the vertebrae to be held at a spacing from each other in order not to cause harm to the spinal cord or nerves.

In principle, it would be conceivable for the at least one distractor-engaging portion to be designed in the form of a projection or lug. However, for reducing the size of the instrument, in particular, an outer diameter of the sleeve, it is expedient for the at least one distractor-engaging portion to be designed in the form of a receiver.

The construction of the receiver can be further simplified by the receiver being designed in the form of a groove.

For improving a secure connection of the distractor and the instrument it is advantageous for the groove to be undercut.

Preferably, the groove has an internal cross section in the form of a T. Thus, distraction forces can be applied in a desired manner without the risk of disengaging the instrument and the distractor.

In accordance with a preferred embodiment of the invention, a first distractor-engaging portion is provided on a distal end portion of the sleeve, and a second distractor-engaging portion is provided on a proximal end portion of the sleeve. Firstly, such a design increases the stability of the system comprising the distractor and the instrument. Secondly, it allows distraction of both end portions of the sleeve individually. This means, for example, that distal end portions of the sleeves connected to two vertebrae can be distracted further than proximal ends of the sleeves. Thus, an inclination of the sleeves can be adjusted in a desired manner.

In order to allow a simple engagement of the instrument and the distractor, it is expedient for the at least one distractor-engaging portion to comprise an insertion opening which is open in proximal direction. Such a design makes it possible to connect the distractor to the instrument by engaging the distractor-engaging portion with a corresponding portion of the distractor by means of a movement of the distractor in a distal direction relative to the instrument.

In accordance with a preferred embodiment of the invention, it is advantageous for the sleeve to comprise at least one first guide member for cooperation with a corresponding second guide member provided on the bone anchorage element head in such a way that the sleeve is engageable with the bone anchorage element in at least one selected position. Such a construction can be expedient, in particular, if special portions or parts of the bone anchorage elements and the instruments are to be aligned for applying the osteosynthesis device to the vertebrae. In particular, it is thus possible to align corresponding recesses of the instrument and the bone anchorage element with each other.

Preferably, the sleeve is provided with an insertion recess at a distal end, the insertion recess being alignable with a connection member receiver of the bone anchorage element head by means of the at least one first and second guide members such that a connection member is insertable through the recess into the connection member receiver. Provision of the insertion recess allows easy access to the connection member receiver for the connection member and a stable and secure connection of the instrument and the bone anchorage element at the same time.

In order to align the sleeve and the bone anchorage element in a desired manner, it is expedient for the at least one first guide member to partially engage the connection member receiver in the at least one selected position. Moreover, such a design reduces the size of the instrument and, in particular, of the bone anchorage element, since no further elements for connection of the bone anchorage element and the instrument are necessary.

To increase the stability of both the connection and the alignment of the sleeve and the bone anchorage element, it is advantageous for the sleeve to comprise two first guide members arranged in diametrically opposed relation to a longitudinal axis of the sleeve. This allows, in particular, insertion of the two first guide members into a slot defining a retainer on the bone anchorage element head.

Furthermore, it is advantageous for the sleeve to comprise a connection member guide for guiding a connection member or a portion thereof into the insertion recess. For example, if the instrument is already connected to the bone anchorage element, the guide facilitates insertion of the connection member into the insertion recess if the insertion recess is not visible for a surgeon. Bringing the guide into contact with the connection member or a portion thereof will automatically lead the connection member into the recess.

In order not to reduce the stability of the instrument, it is expedient for the connection member guide to comprise a shallow guiding recess extending from the insertion recess in proximal direction. This allows contact to be made between the guiding recess and the connection member or a portion thereof and then movements of the connection member in a guided manner into the insertion recess.

Preferably, a proximal end or a proximal end portion of the sleeve is provided with a polygonal external cross section. This allows engagement of, for example, a tool with this portion of the sleeve, in particular, an open-ended wrench for applying a torque to the sleeve. Furthermore, provision of a polygonal external cross section allows application of a torque by either a tool or a distractor. In particular, this portion of the sleeve can also be used as a distractor-engaging portion.

It would be desirable for the instrument to be connectable to the bone anchorage element so that a person does not have to hold the instrument. Therefore, it is advantageous for a clamping mechanism to be provided for keeping the sleeve in a clamped relation with the bone anchorage element in a clamping position. This means that a user of the instrument can release the same after transferring the instrument and the bone anchorage element into the clamping position.

It is advantageous for the clamping mechanism to comprise a clamping member supported on the shaft for clamping the sleeve between the bone anchorage element and the clamping member in the clamping position. Such a construction is particularly simple so that the instrument can be manufactured at low cost.

Furthermore, it is expedient for the shaft to comprise a second externally threaded section at its proximal end, and for the clamping member to be designed in the form of a counter nut which is threadingly engageable with the second externally threaded section of the shaft. Such a design allows clamping of, for example, a sleeve between the counter nut and the bone anchorage element. If the sleeve is engaged with the bone anchorage element in a desired position, the shaft, which is also in engagement with the bone anchorage element, allows application of a clamping force by means of the counter nut to a proximal end of the sleeve, which is thus pushed towards the bone anchorage element.

In accordance with a preferred embodiment of the invention, it is advantageous for a thread pitch of threads of the first externally threaded section to be equal to or larger than a thread pitch of threads of the second tool member. This allows easy insertion of the fixation screw and the first tool member into the threaded section of the bone anchorage element. Such a construction can prevent an undesired clamping or seizing action. Preferably, the thread pitch of threads of the first externally threaded section is equal to the thread pitch of threads of the fixation screw.

It is expedient for a reference element to be provided on the instrument, the reference element being constructed such that it is detectable by a detection device of a navigation system. Provision of such a reference element allows detection of the position and/or the orientation of the instrument, preferably in a three-dimensional space like an operating theater. The navigation system can be, in particular, of the type using electromagnetic radiation for transmitting signals from the reference element to the navigation system and/or vice versa. Moreover, the reference element can be of the type comprising one or more marker elements which are either so-called passive or active markers. Passive markers do not emit radiation of any kind, in particular, electromagnetic waves or ultrasound or the like, actively but merely are designed for reflecting radiation or disturbing an electromagnetic field established in space. Active marker elements can be constructed so as to be able to emit radiation of the types mentioned above. The detection device of the navigation system is preferably of the type for detection of radiation or changes in electromagnetic fields.

It would be conceivable for the reference element to be unreleasably connected to the instrument. However, in order to facilitate cleaning preparing of the instrument for navigation systems of different types, it is advantageous for the reference element to be releasably connectable to the instrument. This allows an easy exchange of reference elements as required. Furthermore, a reference element which is not required can be easily disassembled from the instrument.

Furthermore, in accordance with the invention, it is advantageous to provide an improved osteosynthesis device of the type described hereinabove, wherein at least one of the bone anchorage elements comprises a fixation screw for securing the at least one connection member in the receptacle in a connection position, the device further comprising a first surgical instrument for applying and fixing the fixation screw to a threaded section of the U-shaped receptacle, the instrument comprising a distal end and a proximal end, a first tool member and a second tool member, the first tool member being arranged at the distal end and adapted for engaging the threaded section of the U-shaped receptacle, and the second tool member being adapted for engaging a tool-engaging member of the fixation screw, wherein, in a working position of the instrument, the second tool member is supported on the instrument in a torque proof manner relative to the first tool member about a longitudinal axis and is movable parallel to the longitudinal axis relative to the first tool member.

Such an improved osteosynthesis device allows quick and simple fixation of a connection member to at least two bone anchorage elements fixed to respective vertebrae of the spinal column of a patient's body. Furthermore, such an osteosynthesis device allows the application thereof in minimal invasive surgery.

In order to facilitate the fixation of the bone anchorage element to a vertebrae, it is advantageous for at least one of the at least two bone anchorage elements to be designed in the form of a bone screw.

A connection member can be easily inserted in the U-shaped receptacle of the bone anchorage element if the receptacle forms a head of the bone anchorage element.

Preferably, the first surgical instrument is one of the instruments in accordance with the invention and the described hereinabove.

In principle, it would be conceivable for the connection member to be designed in the form of a plate. However, it is advantageous with a view to easy insertion of the connection member both into the patient's body and into the receptacle provided on the bone anchorage element for the connection member to be designed in the form of a rod. Of course, the connection member can also be designed in the form of a plate having at least one rod-shaped section.

In accordance with a further preferred embodiment, it can be expedient for the device to further comprise a second surgical instrument for holding and inserting the connection member into the U-shaped receptacle.

Preferably, the second instrument comprises a distal end, a proximal end and a first connection portion at the distal end, the first connection portion comprising a connection member receptacle for receiving at least a portion of the connection member, the second instrument further comprising a locking mechanism which is transferrable from a release position, in which the instrument is releasable from the connection member, to a connection position, in which the instrument is connected to the connection member. Such an improved second instrument facilitates both holding and inserting a connection member into the connection member receptacle of the bone anchorage element.

Preferably, the device further comprises a distractor which is connectable to the first instruments for distracting bone parts to which the bone anchorage elements are fixed. Such a distractor allows positioning of at least two vertebrae at a desired spacing from each other.

Moreover, it is advantageous for the device to further to comprise a torque wrench for applying a defined torque to the fixation screw.

The initially stated object is further achieved by a method for fixing an osteosynthesis device on two vertebrae of a spinal column in a minimal invasive manner comprising the steps of minimal invasive accessing the spinal column, fixing at least one anchorage element having a U-shaped receptacle into each of the two vertebrae, inserting a connection member into the U-shaped receptacles with a first instrument, threadingly engaging a fixation screw with the U-shaped receptacles by means of two second instruments, tightening the fixation screws for securing the connection member to the anchorage elements and disengaging the first and second instruments from the connection members and the anchorage elements.

This improved method simplifies fixation of the osteosynthesis device to the two vertebrae. Consequently, it reduces the time of the surgery, which is an advantage for both patient and surgeon.

However, if the vertebrae which are to be connected to each other are not at a desired spacing from each other, it is advantageous for the method to further comprise the step of distracting the vertebrae into a desired position before tightening the fixation screws.

Furthermore, it is expedient for the connection member to be manipulated with the first surgical instrument for holding and inserting the connection member into the U-shaped receptacle, the instrument comprising a distal end, a proximal end and a first connection portion at a distal end, the first connection portion comprising a connection member receptacle for receiving at least a portion of the connection member, the second instrument further comprising a locking mechanism which is transferrable from a release position, in which the instrument is releasable from the connection member, to a connection position, in which the instrument is connected to the connection member. Manipulation of the connection member with such a first surgical instrument allows individual insertion in any direction in a minimal invasive manner. Furthermore, it is impossible to lose the connection member when the first surgical instrument assumes the connection position.

Preferably, the two second surgical instruments are used for applying and fixing the fixation screw to a threaded section of the U-shaped receptacle, the instrument comprising a distal end and a proximal end, a first tool member and a second tool member, the first tool member being arranged at a distal end and adapted for engaging the threaded section of the U-shaped receptacle, the second tool member being adapted for engaging a tool-engaging member of the fixation screw, wherein in a working position of the instrument the second tool member is supported on the instrument in a torque proof manner relative to the first tool member about a longitudinal axis and is movable parallel to the longitudinal axis relative to the first tool member. The use of such second surgical instruments facilitates insertion and fixation of fixation screws to the bone anchorage elements.

In principle, it would be conceivable to connect the second instruments to the bone anchorage elements inside the patient's body. However, to shorten the operation time, it is expedient for the second instruments to be preassembled with the bone anchorage elements before the bone anchorage elements are fixed to the vertebrae. This allows introduction of the bone anchorage elements together with the second instruments into the patient's body and fixing of the anchorage elements to the vertebrae while the second instruments are connected to the bone anchorage elements.

A secure fixation of the osteosynthesis device to the vertebrae is improved if bone screws are used as bone anchorage elements.

Preferably, a rod is used as connection member. Rods can, in particular, be adapted to the curved shape of the spinal column in a desired manner.

BRIEF DESCRIPTION OF THE DRAWINGS

Further objects and advantages of the present invention appear hereinafter in the following description and claims.

The accompanying drawings show, for the purpose of exemplification, without limiting the invention or the appended claims, certain practical embodiments of the present invention, wherein:

FIG. 2 is a longitudinal sectional view of a first instrument for holding and inserting a connection member;

FIG. 3 is an enlarged view of the area A in FIG. 2;

DETAILED DESCRIPTION OF THE INVENTION

Figure 1:
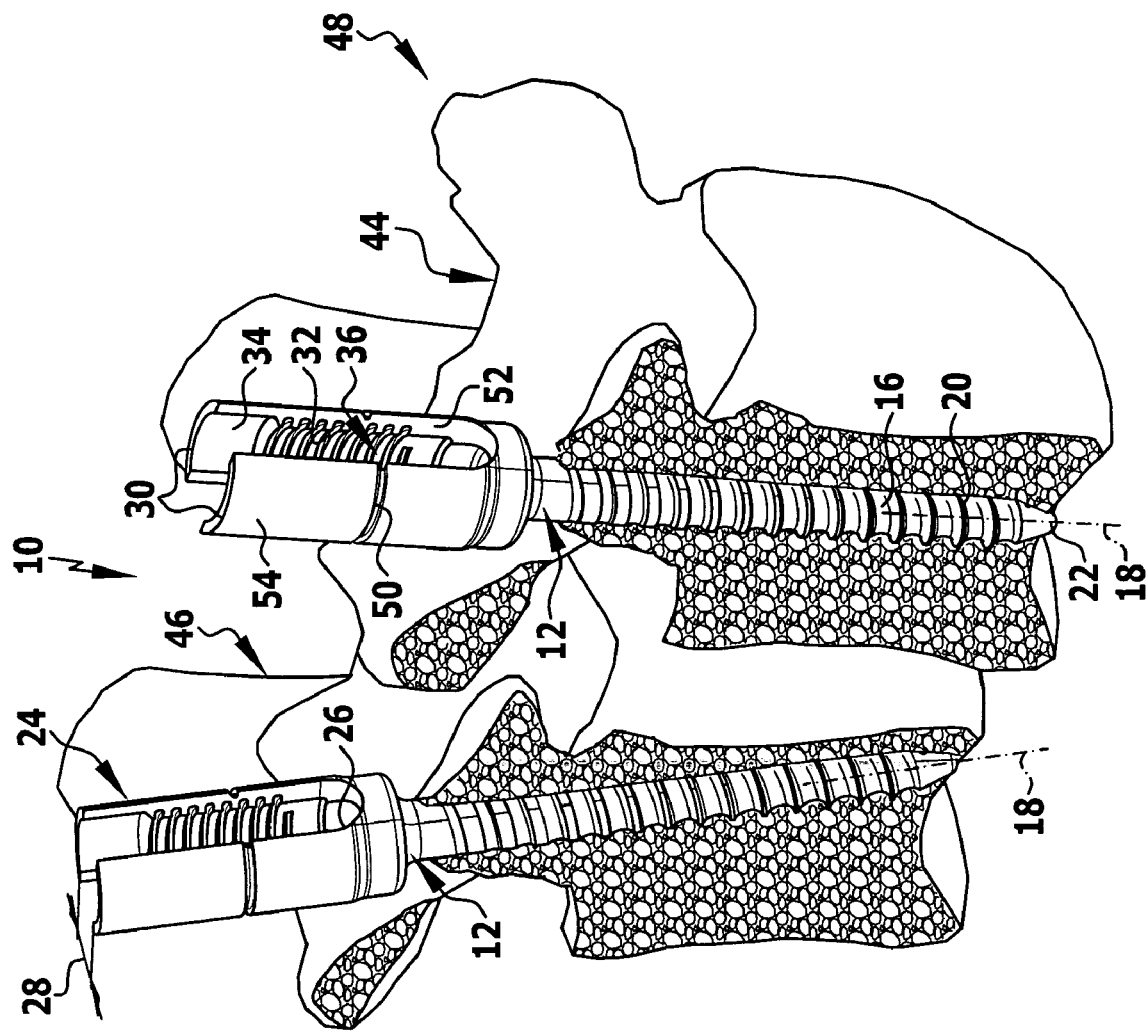
FIG. 1 is a sectional perspective view showing two bone anchorage elements fixed to two adjacent vertebrae.
Figure 4:
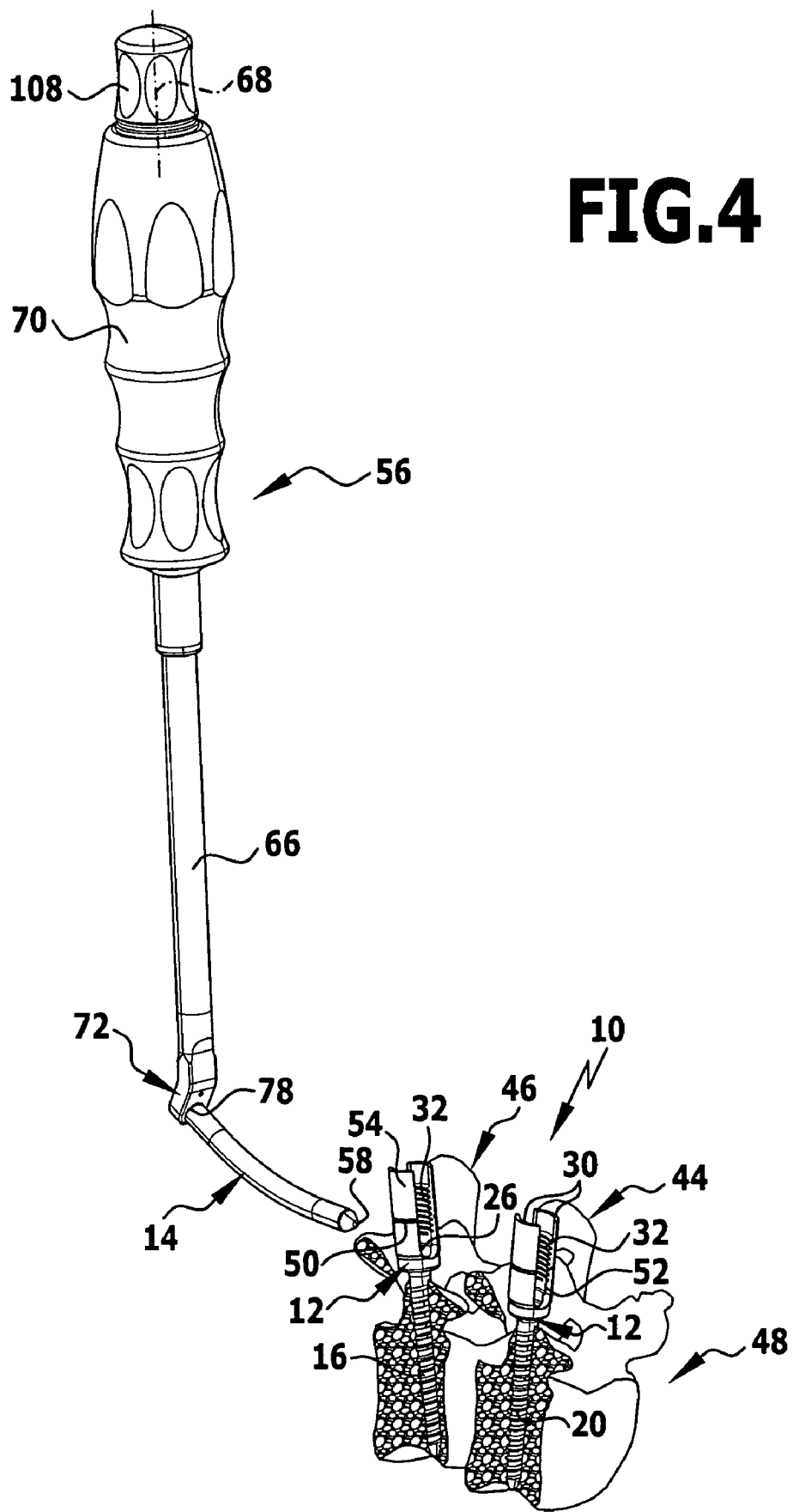
FIG. 4 is a perspective view of the first surgical instrument shown in FIG. 2 while inserting a connection member into retainers of the bone anchorage elements shown in FIG. 1.

An osteosynthesis device 10 shown in the figures comprises at least two bone anchorage elements in the form of pedicle screws 12 and at least one connection member in the form of a curved rod 14 having a substantially circular cross section.

Each pedicle screw 12 comprises an elongated threaded shaft 16 defining a longitudinal axis 18. Threads 20 provided on the shaft 16 can be provided in the form of self-cutting threads. A distal end of the shaft 16 forms a screw tip 22. A proximal end of the pedicle screw 12 forms a bone anchorage element head in the form of U-shaped head or a fork head 24. The fork head 24 is substantially sleeve-shaped and comprises a slot 26 which serves as a connection member seating and can also be called a retainer or a connection member receptacle in which a connection member, for example, a rod 14 or a plate-like element having at least one rod-shaped section, can be seated. The slot 26 has the shape of a semicircle at its closed proximal end with a curvature that matches an outer diameter of the rod 14. In like manner, a width 28 of the slot 26 corresponds approximately to the width or outer diameter of the rod 14. The fork head 24, due to its U-shaped design, comprises two legs having the form of a portion of a cylindrical side wall. Internal threads 32 provided on internal surfaces 34 of the legs 30 define a threaded section 36 to which external threads 38 of a fixation screw 40 correspond so that the fixation screw 40 can be screwed into the threaded section 36 by engaging the external threads 38 in the threads 32 and turning the fixation screw 40 clockwise about the longitudinal axis 18 in distal direction. The fixation screw 40 is designed in the form of a socket screw having a tool-engaging member in the form of a recess 42 which has a hexagonal cross section.

The pedicle screws 12 are screwed into vertebrae 44 and 46 of the spinal column 48 of a human or animal body as, for example, shown in FIG. 1. The legs 30 of the fork head 24 are longer than an external diameter of the rod 14, namely about three to four times longer. This allows simple insertion of the rod 14 into the slot 26. In order to reduce the height of the fork head 24, a predetermined breaking point in the form of a peripheral groove 50 is provided. The groove 50 separates a lower head portion 52 and upper head portion in the form of two tabs 54 defining free ends of the legs 30. The groove 50 is further arranged such that the internal threads 32 are partially provided on the lower head portion 52 and on the tabs 54. After insertion of the rod 14 into the slot 26 the tabs 54 can simply be broken away in a defined manner because of the groove 50.

The rod 14 can be inserted by a surgeon either by hand or by means of a rod insertion instrument 56. The rod 14 is curved with a first free end in the form of a blunt tip 58 and a second free end 60 having a multi-sided shape with a polygonal cross section, preferably a hexagonal or octagonal cross section. The rod 14 is slightly curved so that longitudinal axes 62 and 64 defined by the tip 58 and the end 60 are inclined relative to each other about an angle of about 25°.

The rod insertion instrument 56 comprises an elongated hollow shaft 66 defining a longitudinal axis 68. A proximal end of the shaft 66 is surrounded by an ergonomically designed handle portion 70 which allows an ergonomic grasping of the instrument 56 by a surgeon or a surgical nurse. A distal end of the shaft 66 defines a first connection portion 72 which defines a further longitudinal axis 74, which is inclined relative to the longitudinal axis 68 about an angle of about 30°. The first connection portion 72 has an opening 76 which is opened in distal direction and arranged concentrically about the longitudinal axis 74. In a direction transverse in relation to the longitudinal axis 74 the first connection portion is provided with a through-hole 78 which forms a connection member receptacle for receiving at least a portion of the rod 14, for example, the rod's end 60. The through-hole 78 is of internal multi-sided shape. Inner edges of the through-hole 78 can be rounded so that the through-hole 78 assumes the shape of a so-called torx® tool. The through-hole 78 is dimensioned such that the end 60 can be inserted into the through-hole 78 parallel to its longitudinal axis 64, i.e. in a direction transverse to the longitudinal axis 74. Outer dimensions of the end 60 do not exactly correspond to the dimensions of the through-hole. Preferably, there is a small amount of play between the end 60 and the through-hole 78 when the end 60 is inserted in the through-hole 78.

In order to secure the rod 14 on the instrument 56 provision is made for a locking mechanism 80 to be arranged on the instrument 56. The locking mechanism 80 comprises a locking member 82 which is movably supported on the shaft 66. The length of the locking member 82 corresponds to about half of the length of the first connection portion 72. The locking member 82 is of substantially cylindrical shape having a peripheral groove 84 which defines circular stop surfaces 86 and 88 pointing in distal and proximal direction. A stop member 90 is arranged on the first connection portion 72 such that it projects at least partially from an internal side wall 92 of the first connection portion 72 into the groove 84. The stop member 90 can, in particular, be formed by a set screw having an outer diameter which is smaller than a width of the groove 84 parallel to the longitudinal axis 74. This allows the locking member 82 to move or to be moved from the most distal position, in which the stop surface 86 pointing in distal direction abuts on the stop member 90, to a most proximal position, in which the stop surface 88 pointing in proximal direction abuts on the stop member 90.

Although not shown in the figures, the locking member 82 can be biased in proximal direction by means of a bias member, for example, a spring. This results in a constrained movement of the locking member 82 in proximal direction. Such a bias member constrains the locking member 82 to assume its most proximal position which, thus, defines a normal position of the locking mechanism 80 or the instrument 56. In the normal position, a distal end surface 94 of the locking member 82 does not project into the through-hole 78.

However, the end surface 94 can be forced in distal direction to abut on a surface 96 of the end 60 to key clamp the end 60 on the first connection portion 72, i.e., the instrument 56 then assumes a connection position. If the locking member 82 is moved in proximal direction, the side surface 96 and the end surface 94 disengage so that the end 60 can be released from the first connection portion 72, i.e. the instrument 56 then assumes a release position.

The locking mechanism 80 further comprises a transmission member 98 in the form of an elongated cylindrical rod which is provided with a short section of external threads 100 in the region of its distal end 102. The distal end 102 has substantially the form of a semisphere. An inner section of the shaft 66 next to the first connection portion 72 is provided with internal threads 106 which correspond to the external threads 104. A proximal end of the transmission member 98 extends beyond a proximal end of the handle portion 70 and is connected in a torque proof manner to an actuation member in the form of a knob 108. For guiding the transmission member, a so-called "luerlock" is provided on the proximal end of the shaft 66 and extends at least partially in proximal direction beyond the handle portion 70. The "luerlock" forms a standard irrigation adapter which can be connected to an irrigation source, for example, by means of a hose or the like and which is in fluid communication with the interior of the shaft 66. The adapter 110 facilitates cleaning of the instrument 56 after disassembling the transmission member 98.

The transmission member 98 can be inserted into the shaft 66 by inserting the end 102 through the adapter 110 into the interior of the shaft 66 until the threads 106 enter into contact with the threads 104. Then, a further axial movement of the transmission member 98 in distal direction requires a turning movement of the transmission member 98 about the longitudinal axis 68 clockwise so that the end 102 proceeds towards a proximal end 112 of the locking member 82. As soon as the end 102 gets into contact with the proximal end surface 112 pointing in proximal direction, further movement of the transmission member 98 in distal direction urges the locking member 82 in distal direction and allows clamping of the end 60 in the through-hole 78. Thus, turning the knob 108 allows transfer of the instrument 56 from the release position, in which the end 60 can be introduced into the through-hole 78 and retracted therefrom, to a connection position, in which the end 60 is securely held in the through-hole 78 in a clamped manner. A connection position of the instrument 56 is shown, in particular, in FIGS. 2 and 3.

Figure 5:
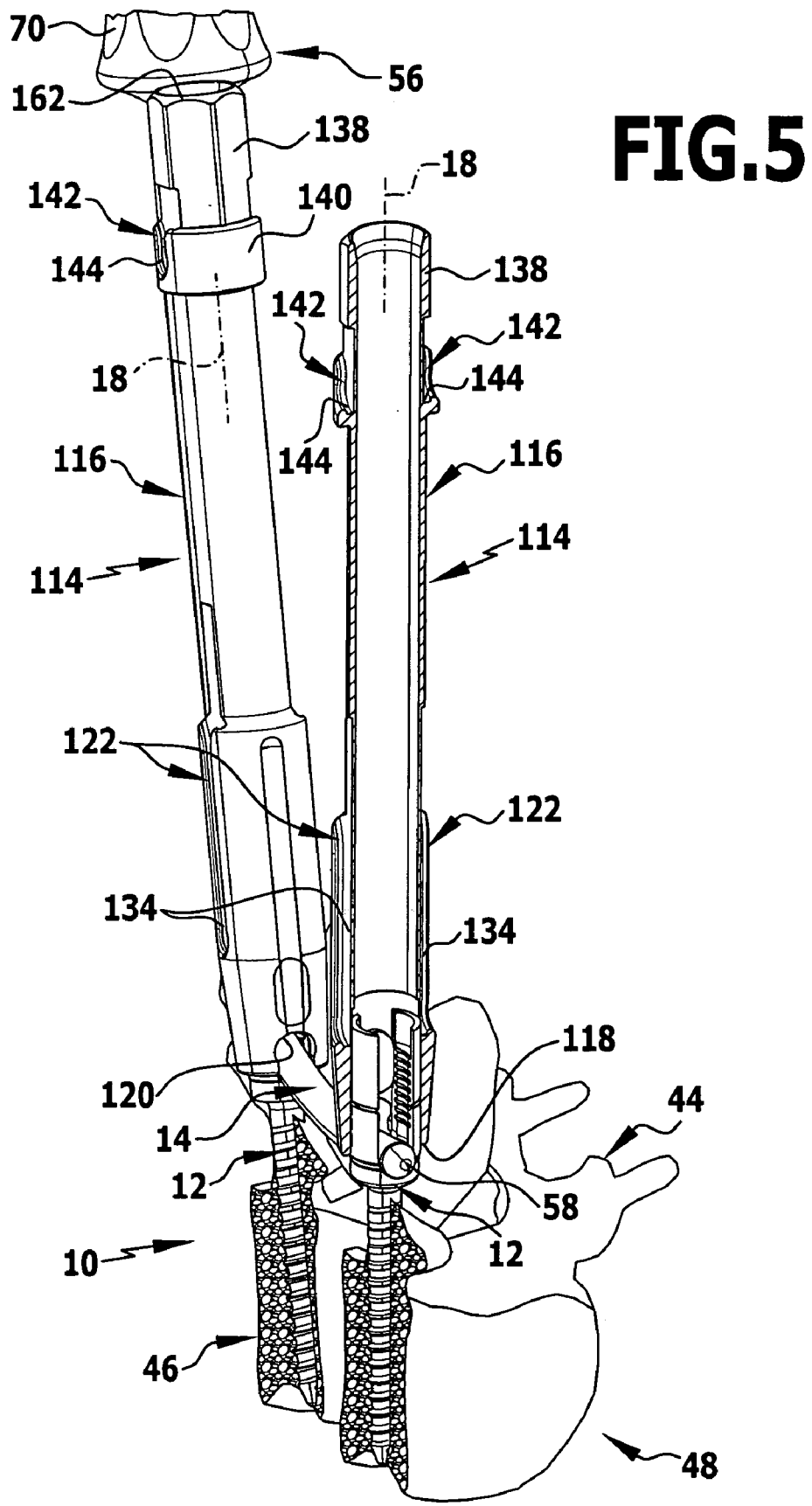
FIG. 5 is a partially sectional perspective view of a connection member inserted into a retainer of the bone anchorage elements and held with the first instrument.
Figure 6:
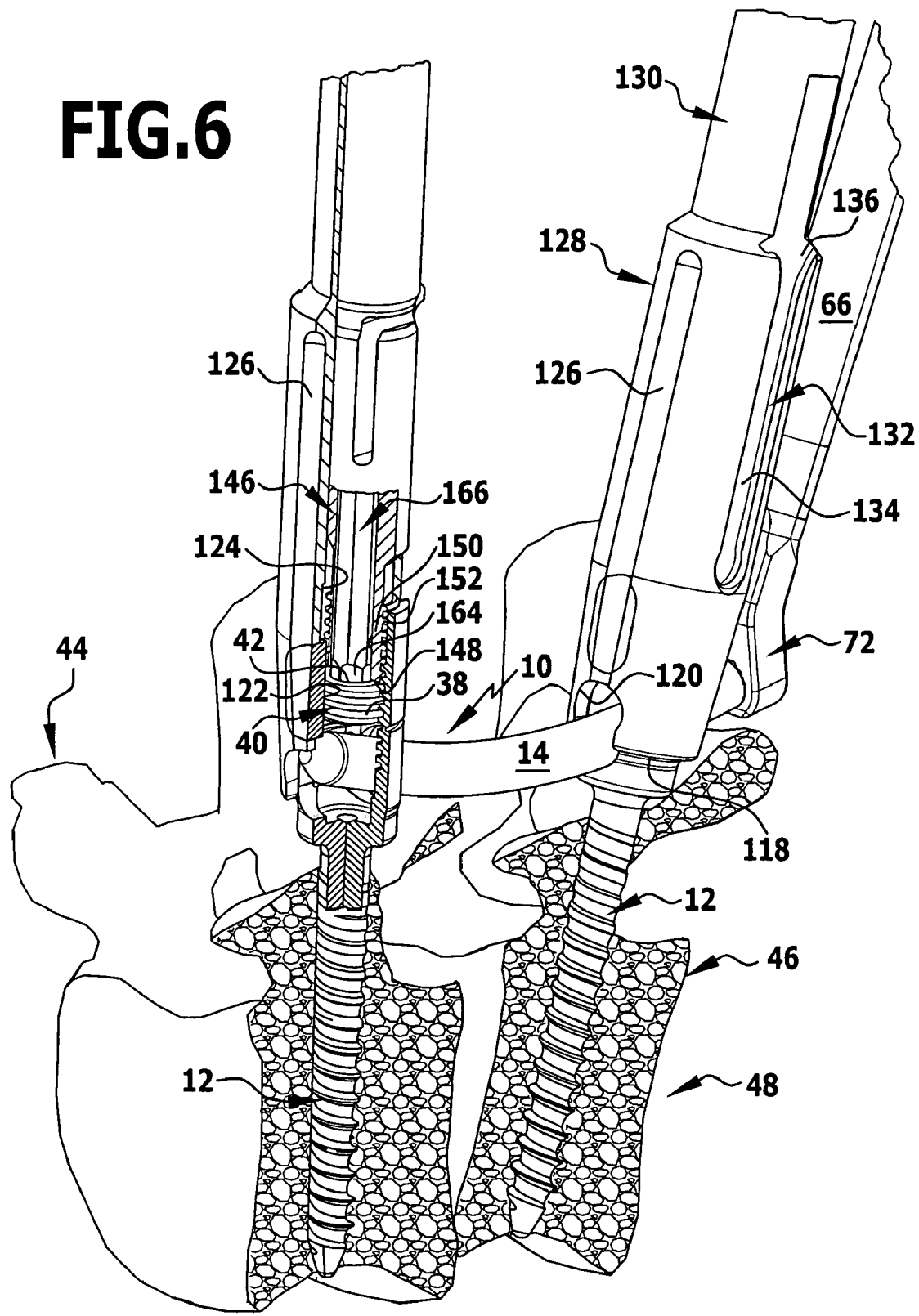
FIG. 6 is a partially sectional perspective view of the scenario shown in FIG. 5 further showing second instruments for applying fixing screws to the retainers of the bone anchorage elements.

When the rod 14 is securely held on the instrument 56 in the connection position, a surgeon can easily introduce the curved rod 14 into the slots 26 of the fork heads 24 of the pedicle screws 12. It is even possible to apply a torque to the rod 14 by means of the instrument 56, which facilitates insertion of the rod into the patient's body and through surrounding tissues towards and into the slots 26. After insertion of the rod 14 into the slots 26 with the instrument 56 the rod is held in the desired position by means of the instruments as shown in FIGS. 5 and 6.

In a next step a further surgical instrument 114 is used for guiding the fixation screw 40 into the fork head 24 and screwing in the fixation screw 26 for fixing the rod 14 to the fork head 24 of the pedicle screw 12. The surgical instrument 114 comprises a longitudinally extending tubular outer sleeve 116 which can be connected to the fork head 24 in such a way that a longitudinal axis 18 defined by the sleeve 116 coincides with the longitudinal axis 18 of the screw 12.

Two insertion recesses 120 extending from a distal end 118 of the sleeve 116 in proximal direction are provided symmetrically and in diametrically opposed arrangement in relation to the longitudinal axis 18. The insertion recesses 120 are dimensioned such that they are adapted to receive the rod 14 and to form a proximal stop effective in proximal direction for the rod 14.

In order to facilitate alignment of the insertion recesses 120 and the slots 26, two first guide members 122 are provided on the sleeve 116. The guide members 122 are inserted in a side wall of the sleeve 116 and protrude beyond an inner wall surface 124 of the sleeve 116 so that they can engage the slots 26 when the sleeve 116 is moved over the fork head 24 in distal direction. The first guide members 122 are arranged in the vicinity of the insertion recesses 120 but proximal thereof. As can be seen, for example, in FIG. 6, the first guide members 122 engage the slots 126 between the tabs 54.

On the exterior of the sleeve 116 two shallow grooves 126 are provided which extend from the insertion recess 120 parallel to the longitudinal axis 18 in proximal direction over a length which corresponds substantially to the length of a distal end portion 128 of the sleeve 160. The distal end portion 128 has a larger diameter than a sleeve-like centre portion 130 of the sleeve 116 which extends in proximal direction starting from the distal end portion 128. The distal end portion 128 further comprises two distractor-engaging portions 132 in the form of undercut grooves 134 having a cross-sectional shape in the form of a T. A distal end of the groove 134 is closed, whereas a proximal end of the groove 134 is provided with an insertion opening 136. The grooves 134 extend parallel to the longitudinal axis 18 over a length defined by a distance between a transition region, defined between the distal end portion 128 and the centre portion 130, and proximal ends of the first guide members 122. The grooves 134 are arranged diametrically opposed in relation to the longitudinal axis 18 but displaced about an angle of rotation of 90° with respect to the insertion recesses 120.

Figure 8:
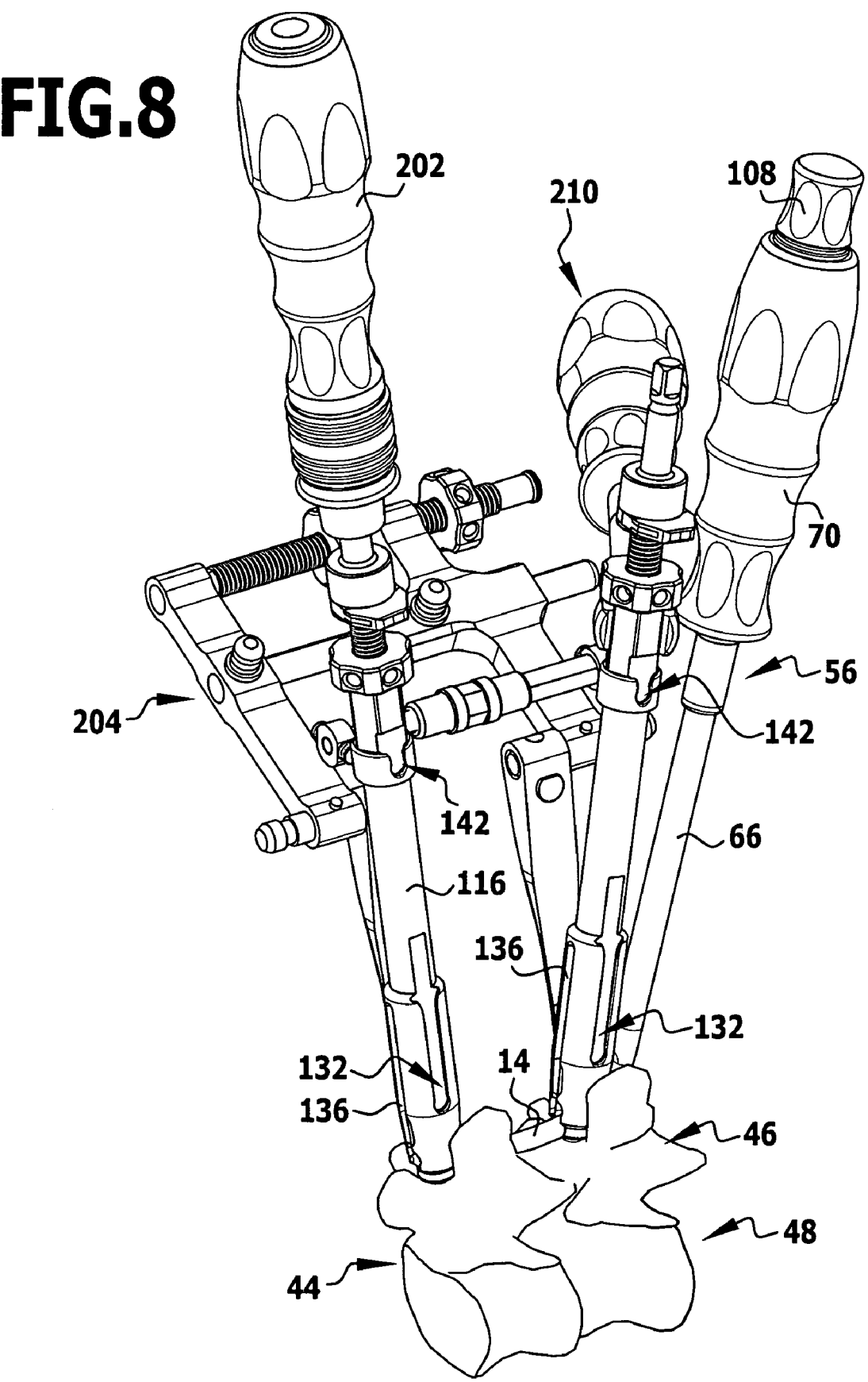
FIG. 8 is a perspective front elevational view of an osteosynthesis device applied by means of first and second surgical instruments connected to a distractor for positioning the vertebrae in a desired relative position.
Figure 9:
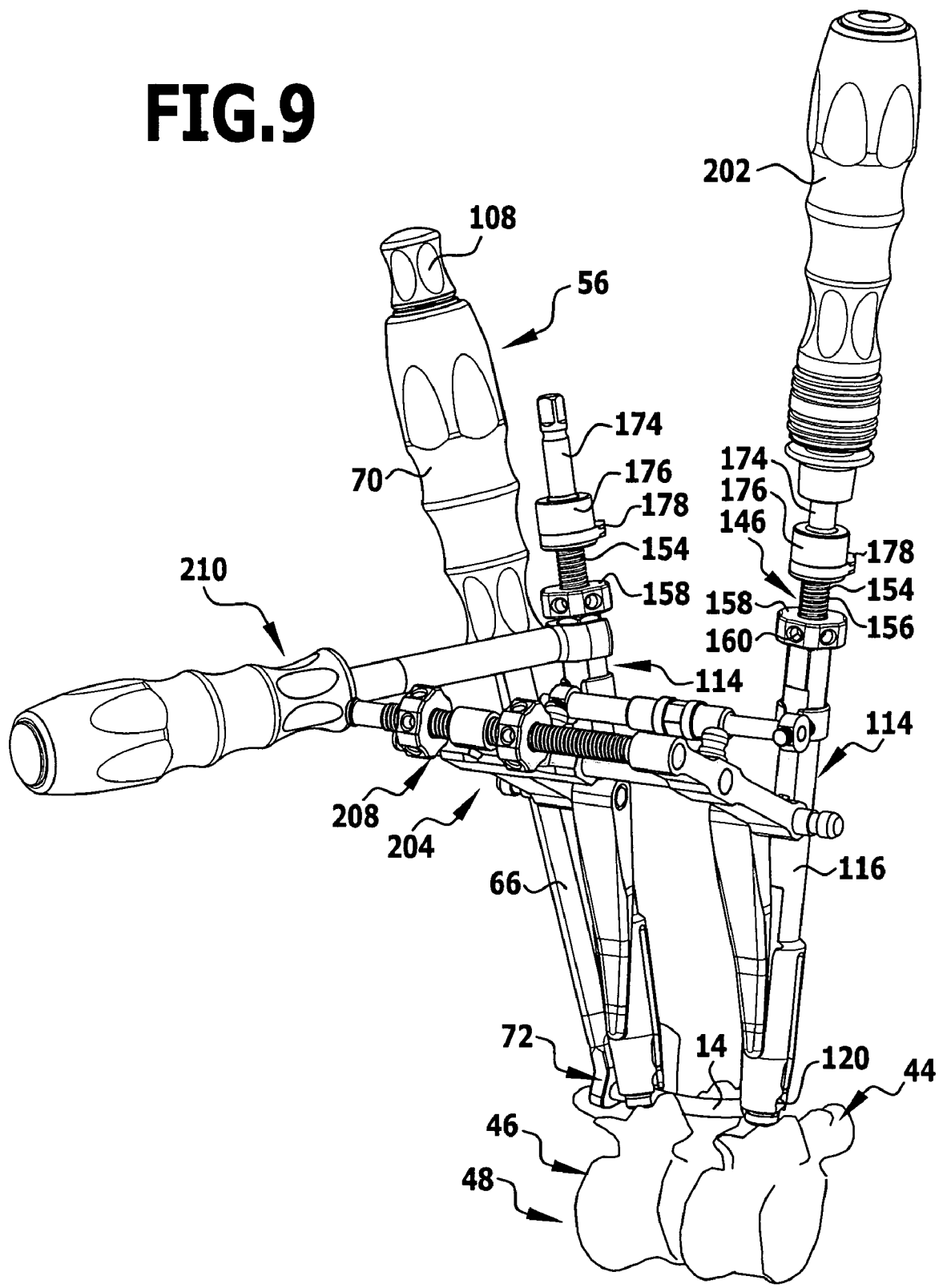
FIG. 9 is a back perspective elevational view of the arrangement shown FIG. 8.
Figure 10:
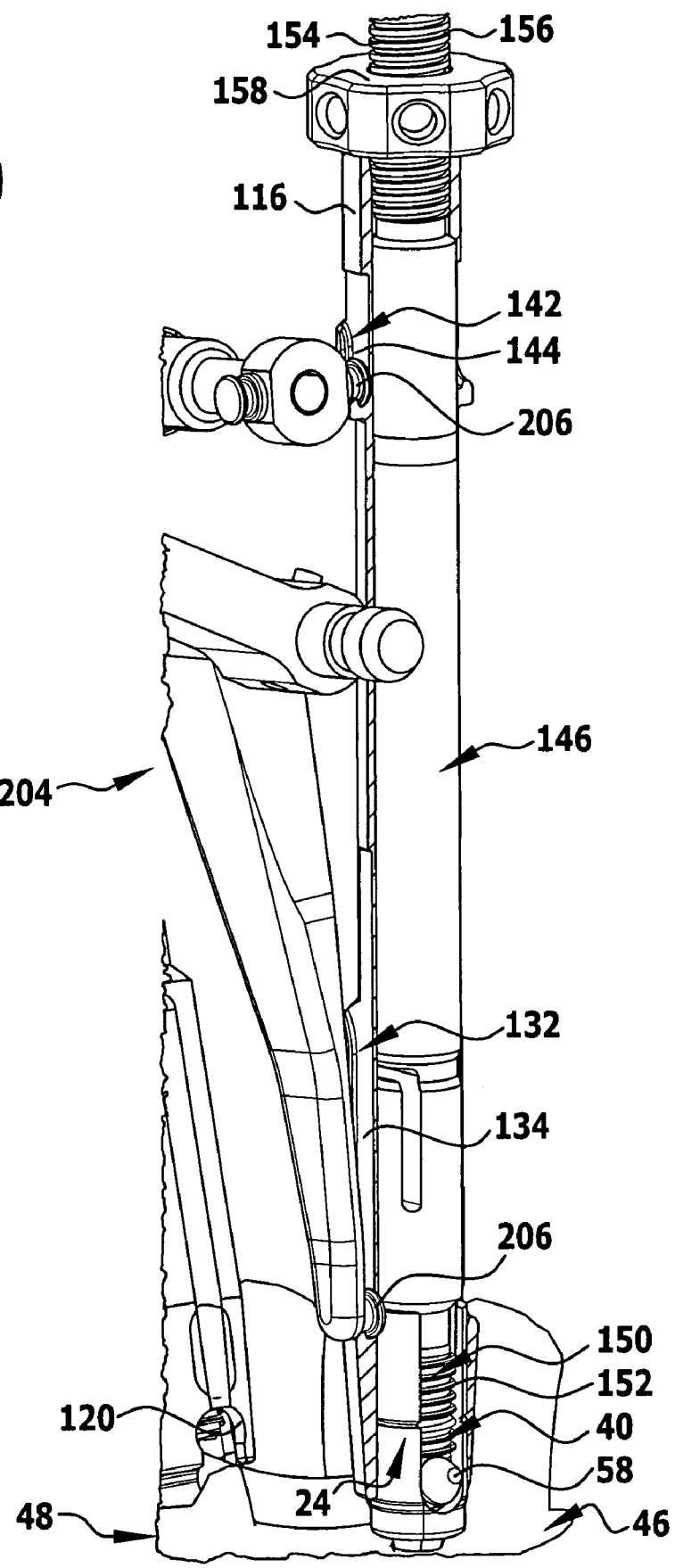
FIG. 10 is a partially sectional perspective view of one of the second instruments showing the connection of the second instrument to the distractor.
Figure 11:
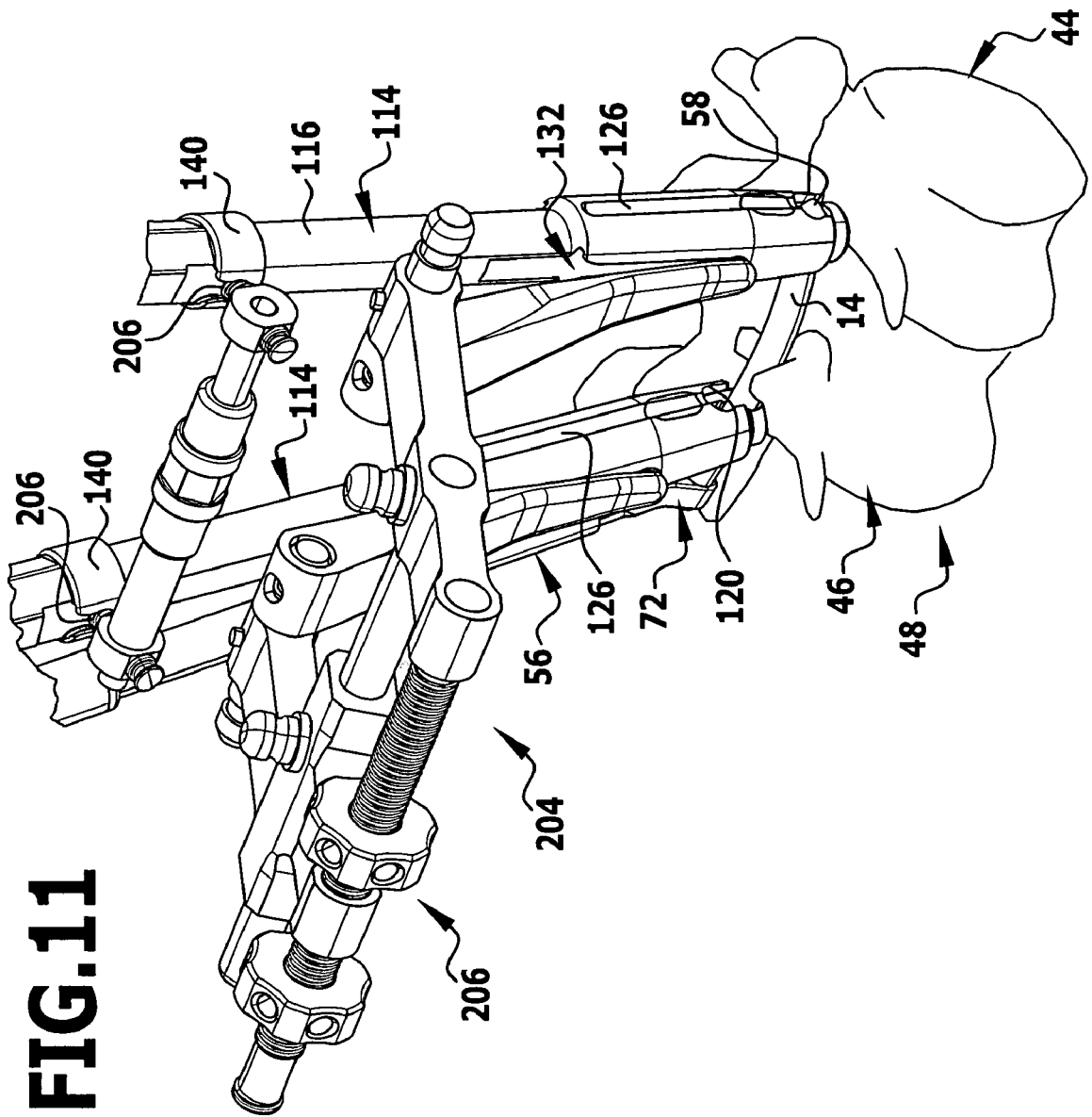
FIG. 11 is an enlarged back perspective view of the distractor shown in FIGS. 8 through 10.
Figure 12:
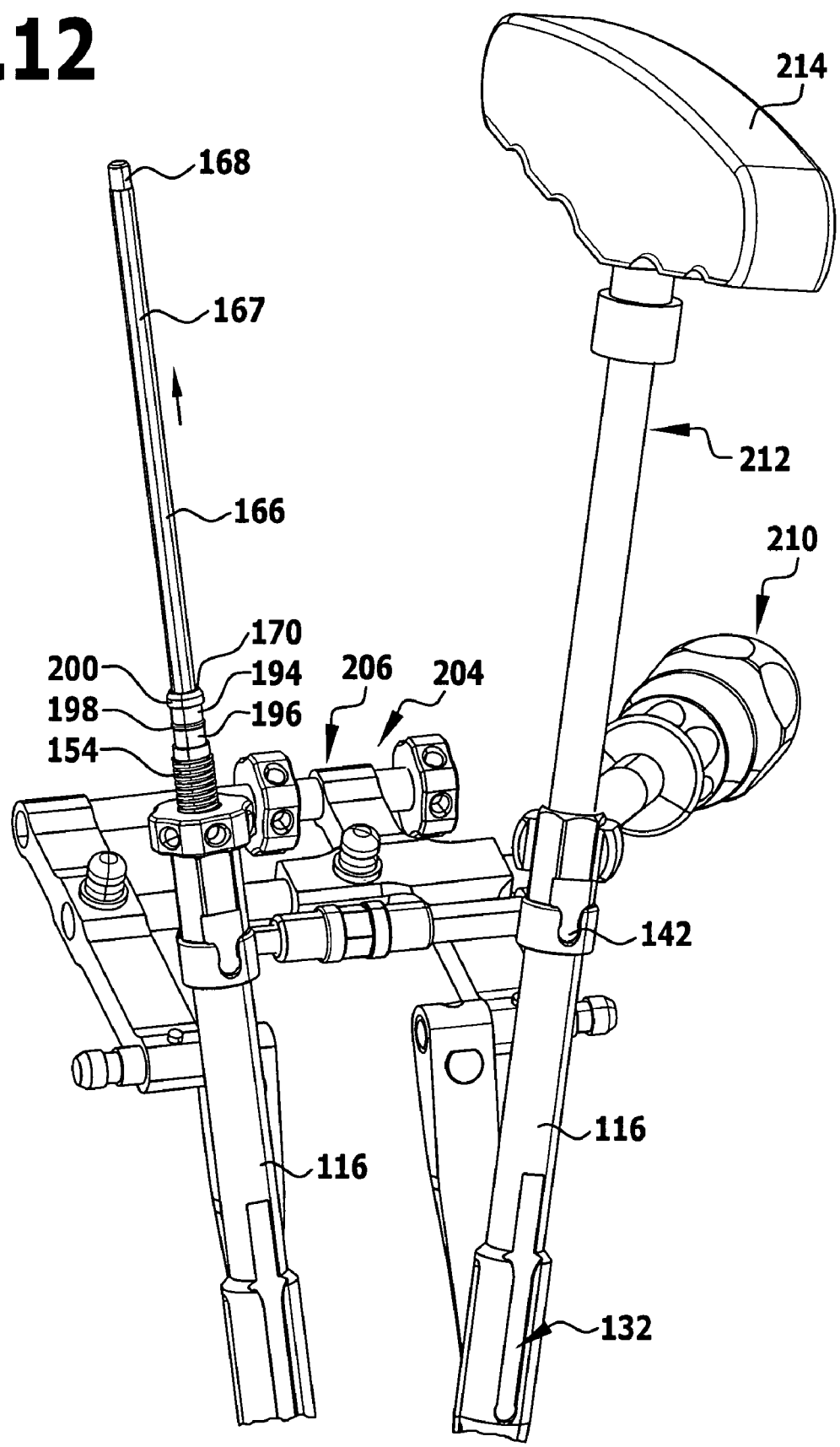
FIG. 12 is a front perspective elevational view taken while tightening the fixing screws with a torque wrench.
Figure 13:
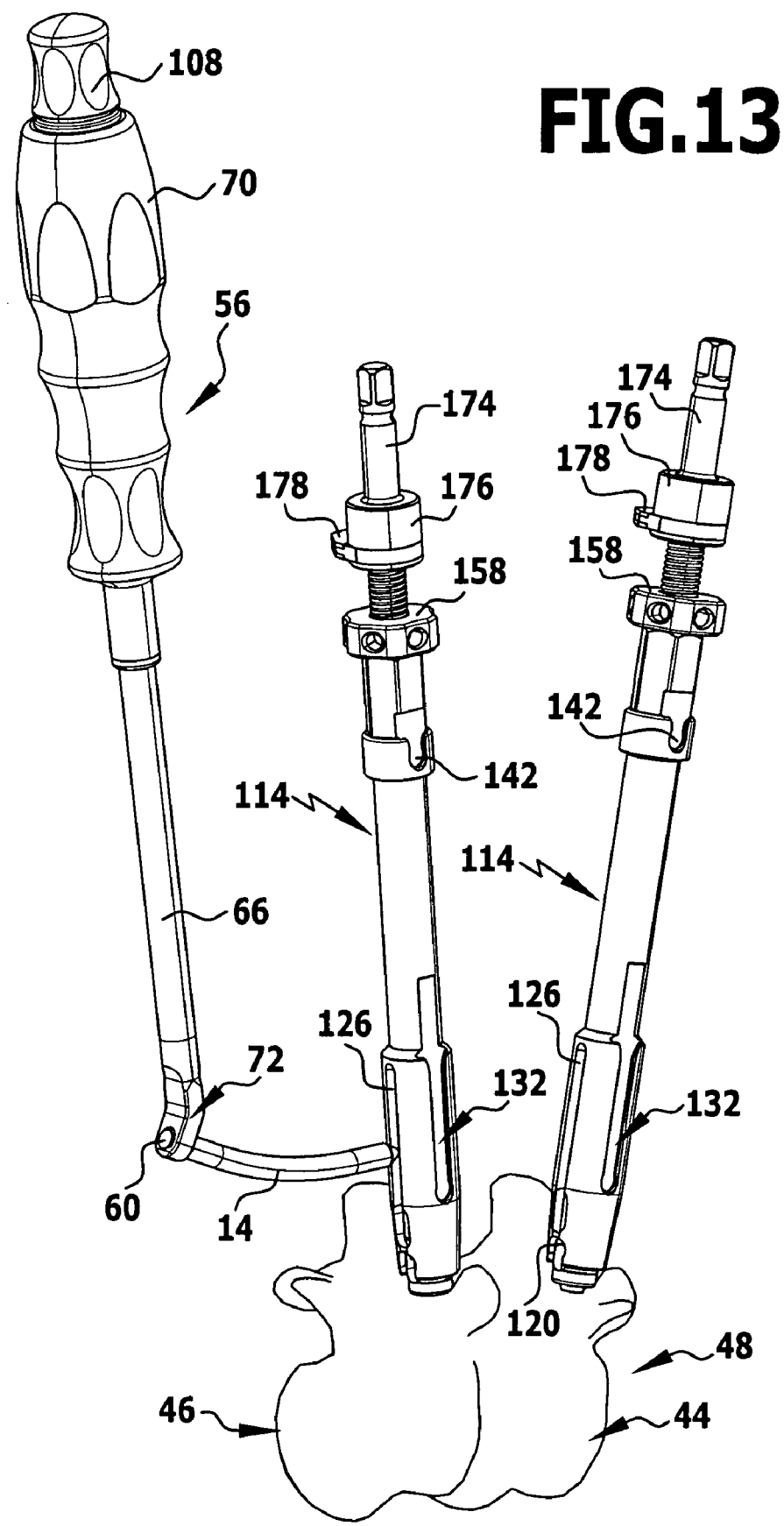
FIG. 13 is a perspective view of the osteosynthesis device taken while inserting the connection member with the first instrument into the retainers of the bone anchorage elements with the second instruments already connected to the bone anchorage elements.

A proximal end of the sleeve 116 has an external noncircular cross section of polygonal shape, namely of hexagonal shape. It forms an end portion 138 of multisided shape which can be engaged by an open-ended wrench, for example, a wrench 210 as shown in FIGS. 8, 9 and 12.

On a distal side of the end portion 138 the outer diameter of the sleeve 116 increases in one step and forms a ring-like peripheral projection 140. Second guide members 142 are provided on the projection 140 in the form of two undercut grooves 144 which are closed in distal direction and open in proximal direction. The grooves 144 extend parallel to the longitudinal axis 18 and are aligned with corresponding grooves 134 forming the first guide member 122.

The surgical instrument 114 further comprises a first hollow shaft 146 which is dimensioned such that it can be introduced into the sleeve 116 through the end portion 138. A distal end 148 of the shaft 146 is provided with an externally threaded section 150 comprising threads 152 which correspond to the external threads 38 of the fixation screw 40. Consequently, the threads 152 also correspond to the internal threads 32 of the fork head 24. After insertion of the shaft 146 into the sleeve 116 the externally threaded section 150 can be threadingly engaged with the threads 32. The externally threaded section 152 forms a first tool member of the instrument 114. Moreover, the shaft 146 has a further externally threaded section 154 arranged in the region of its proximal end and comprising threads 156. A counter nut 158 is threadingly engaged with the externally threaded section 154. The counter nut 158 has a substantially hexagonal outer cross section with blind bores 160 whose longitudinal axes point radially away from the longitudinal axis 18. The counter nut 158 serves for clamping the sleeve 116 to the pedicle screws 12. For that purpose, a distal side surface of the nut is brought into contact with a proximal end surface 162 of the end portion 138. Further clockwise turning of the counter nut 158 clamps the sleeve 116 between the counter nut 158 and the rod which is inserted into the slot 26 when the shaft 146 threadingly engages the fork head 24.

The surgical instrument 114 further comprises a second tool member 164 which is formed by a multi-sided end portion of an elongated shank 166. The second tool member 164 has an outer non-circular cross section of polygonal shape, preferably of hexagonal shape. The second tool member is designed to correspond to the recess 42 of the fixation screw 40. The shank 166 has a shaft-engaging portion 167 which also has a non-circular cross section of polygonal shape and extends almost over the entire length of the shank 166. The shank 166 has a length so that a proximal end 168 extends beyond a proximal end 170 of the shaft 146. The cross section of the shank 166 is preferably of hexagonal shape but can also be, as shown in FIG. 6, of octagonal shape. The shank 166 can be introduced into the shaft 146 through the end 170.

Since an inner cross section of the shaft 146 corresponds to the outer cross section of the shaft engaging portion 167 of the shank 166 the shank can be inserted into and moved relative to the shaft 146 parallel to the longitudinal axis 18. Moreover, the shank and the shaft are thus supported on the instrument 146 in a torque proof manner relative to each other. This means that a turning action applied to the shank 166 results in a constrained rotary movement of the shaft 146.

Furthermore, the shank 166 and the shaft 146 can be brought into and locked in a defined axial relation. For this purpose, a locking mechanism 172 is provided. The proximal end 168 is connected to a handle adapter 174 in a torque proof manner. The handle adapter 174 has a distal end portion 176 which surrounds a proximal end portion of the shaft 146 in a sleeve-like manner. The end 170 forms a stop for an internal circular surface pointing in distal direction of the handle adapter 174.

Figure 7:
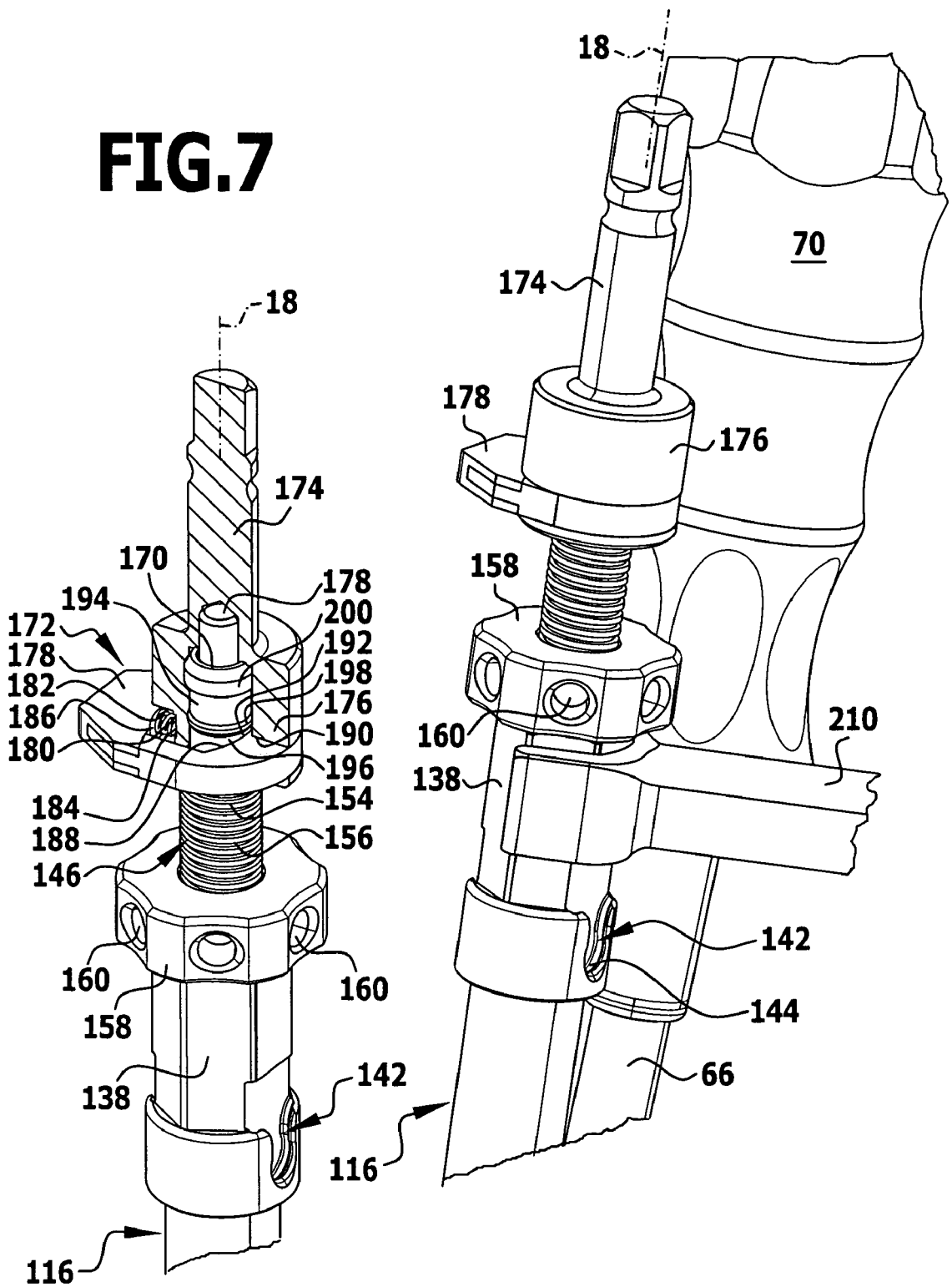
FIG. 7 is a partially sectional view of proximal ends of the second instruments which are partially shown in FIG. 6.

A first locking member 178 is supported on the end portion 176 and movable in a direction transverse to the longitudinal axis 18. The locking member 178 is designed substantially in the form of a push button, which is held in a locking position, as shown in FIG. 7, by means of a bias member in the form of a coil spring 180. The coil spring 180 is supported on the one hand on the bottom surface 180 of a blind bore 182 whose longitudinal axis extends transversely to the longitudinal axis 18. The coil spring 180 is supported on the other hand on an inner surface 186 of the locking member 178 pointing towards the longitudinal axis 18. The locking member 178 is provided with a through-hole 188 such that the substantially plate-like locking member 178 surrounds the shaft and engages a slot 190 of the end portion which is diametrically opposed to the side surface 186 which forms a portion of an inner wall of the through-hole 188. As a result of the design of the locking mechanism 172, the coil spring 180 pushes the side surface 186 away from the longitudinal axis 18, so that a side surface 192 of the through-hole 188 which is substantially diametrically opposed to the side surface 186, is moved towards the longitudinal axis 18. Due to the coil spring 180 the locking mechanism 172 assumes a locking position as a normal position.

For locking the shank 166 to the shaft 146, the shaft 146 is provided with two ring grooves 194 and 196 which are separated by a peripheral projection 198. The ring groove 194 is arranged adjacent to a ring flange 200 which defines the proximal end 170 of the shaft 146. The projection 198 limits the ring groove 194 on a distal side and the ring groove 196 is arranged adjacent to the projection 198 on a distal side thereof. The ring grooves 194 and 196 form second locking members of the locking mechanism 172. Further, the ring groove 196 is limited distally by the externally threaded section 154.

A width of the ring grooves 194 and 196 parallel to the longitudinal axis 18 is a little bit larger than the thickness of the plate-like locking member so that the locking member 178, which is guided in the slot 190, can enter into contact with one of the two grooves 194 with its side surface 192. The shank 166 is secured on the shaft 146 when the locking member 178 engages one of the ring grooves 194 or 196. For disengaging, the shank 166 and the shaft 146, the locking member 178 has to be moved against the force exerted by the coil spring 180 so that the side surface 192 releases the ring groove 194 or 196.

The locking mechanism 172 is now in a release position, which allows withdrawal of the shank 166 in proximal direction.

The ring groove 196 defines a first locking position, in which the second tool member 164 extends beyond a distal end of the shaft 146. The ring groove 194 defines a second locking position, in which the shank 166 is retracted into the shaft 146 and brought out of engagement with the fixation screw 40 when the locking member 178 engages the ring groove 194.

The handle adapter 174 can be releasably connected to a handle 202, preferably in the form of ratchet. This allows an easy rotary movement of the shank 166 both clockwise and counter clockwise.

For applying the fixation screw 40 to the fork head 24, the instrument 114 is preassembled as follows. In a first step, the shank 166 is inserted into and locked to the shaft 146 in the first locking position, in which the second tool member 164 extends beyond the distal end 148. The fixation screw 40 is then connected to the second tool member 164 by introducing the same into the recess 42. Now, the shank 166 connected to the shaft 146 can be introduced together with the shaft 146 through the sleeve 116 and moved forward in distal direction until the external threads 38 of the fixation screw 40 contact the threads 132. Rotation of the handle 202 connected to the shank 166 threadingly engages both the fixation screw 40 and the externally threaded section 152 with the threaded section 36 of the fork head 24.

The pitch of the external threads 38 corresponds to the pitch of the threads 152 so that the fixation screw 40 cannot block the threaded engagement of the externally threaded section 150 and the threads 32. In order to facilitate the engagement of the threads 152 and the threads 32 after screwing in the fixation screw 40 into the fork head 24, the ring groove 196 is a little bit wider than the thickness of the locking member 178 parallel to the longitudinal axis 18 so that sufficient play is provided for leading a free end of the threads 152 into the threads 32. As described above, the screw 40 can be screwed in until it contacts the rod 14 inserted in the slot 26. Further turning of the shank 166 results in a pretightening action which secures the rod 14 to the pedicle screw 12.

With a further second surgical instrument 114 the rod 14 can be secured to the pedicle screw 12 in the same way.

In order to position the vertebrae 44 and 46 in a desired position relative to each other, a distractor 204 is provided, which can be connected to the instruments 114 which are clampingly secured to the pedicle screws 12 as shown, for example, in FIGS. 8, 9, 11 and 12. For this purpose, the distractor 204 is provided with at least four adapters 206 which are identically designed in the form of plate-like projections which can be introduced into the distractor-engaging portions 132 and into the second guide members 142. The distractor 204 further comprises a drive mechanism 208 which allows adjustment of a distance between the adapters 206 which are engaged with the instruments 114 in such a way that a distance between the surgical instruments 114 and an inclination between the same can be adjusted in a desired manner. In particular, the distractor 204 can be used to move the vertebrae 44 and 46 away from each other to release pressure exerted on the spinal cord. The distractor 204 is substantially known in the art, however, the adapters 206 are new since grooves 134 and 144 on the sleeve 116 reduce a maximum diameter on the sleeve 116. This has the further advantage that a smaller access to the patient's body is required for introducing the instrument 114 into the body.

Further, a flat ended wrench 210 can be provided for engaging the end portion 138 of the sleeve, which allows turning of the sleeve 116 as a whole together with the pedicle screw 12 secured thereto.

When the vertebrae 44 and 46 are positioned as desired, the fixation screws 40 are pretightened such that the rod 14 is secured to the pedicle screws 12. The rod 14 is still connected to the instrument 56. In a next step, the locking mechanism 172 is transferred from the first locking position to the second locking position in which the second tool member 164 is retracted into the shaft 146. Now, the shank 166 and the shaft 146 are still locked relative to each other but assume the second locking position. This allows unscrewing of the shaft 146 from the fork head 24 without unscrewing the fixation screw 40 since the second tool member 164 and the recess 42 are disengaged. After unscrewing the shaft 146 from the fork head 24 the shaft 146 is retracted from the sleeve 116.

In a next step, the fixation screw 40 can be tightened with a defined torque by use of a torque wrench 212 whose distal end engages the recess 42 and which has a proximal end in the form of a T-bar 214. The T-bar can be grasped by hand and turned for fixing the fixation screw 40 into the fork head 24.

Afterwards, the torque wrench 212 is retracted and the locking mechanism 80 of the instrument 56 can be transferred from the connection position to the release position, which allows removal of the instrument 56 from the rod 14. Finally, the distractor 204 and the sleeves 116 are withdrawn from the fork heads 24.

Before closing the access to the patient's body, the tabs 54 of the pedicle screws 12 are broken off and removed from the patient's body.

The method for fixing the osteosynthesis device 10 on the vertebrae 44 46 of the spinal column 48 in a minimal invasive manner comprising the steps of minimal invasive accessing the spinal column, fixing a pedicle screw having a fork head 24 into each of the two vertebrae 44 and 46, inserting the rod 14 into the slots 26 by means of the instrument 56, threadingly engaging the fixation screw 40 with the fork head 24 by means of the instrument 114, tightening the fixation screws 40 for securing the rod 14 to the pedicle screws 12 and disengaging the instruments 56 and 114 from the rod 14 and the pedicle screws 12, can be at least partially modified.

Alternatively, the instrument 114 can be mounted on the pedicle screw 12 before screwing the pedicle screw 12 into one of the vertebrae 44 or 46. For preassembling the unit comprising the instrument 114, the pedicle screw 12 and the fixation screw 40, the sleeve is moved over the fork head 24 and a subunit comprising the shaft, the shank and the fixation screw preassembled as described above, is introduced into the sleeve 116. By means of the counter nut 158 the instrument 114 can be tightly clamped to the pedicle screw 12.

Now, since the instrument 114 is connected to the pedicle screw 12 in a torque proof manner, the pedicle screw 12 can be screwed into the vertebrae 44 or 46 by means of the instrument 114. For this purpose, the instrument 114 can be, for instance, connected to the handle 202.

In a next step, the rod 14 has to be inserted into the slots 26 of the pedicle screw 12. The shallow grooves 126 on the sleeve 116 simply insertion of the rod 14 into the slot 26. The surgeon moves the rod 14 with its tip 58 towards the sleeve 116 in order to engage the tip 58 and the shallow groove 126. As soon as the tip 58 is guided in the shallow groove 126, the surgeon has only to move the instrument 56 parallel to the longitudinal axis 18 and the tip 58 is automatically guided into the recess 120. Now, the surgeon can move the instrument 56 transversely to its longitudinal axis 68, which moves the rod 14 into the slot 26. Pushing the rod 14 through the slot 26 moves the tip 58 out of the slot 26 on its other side and the surgeon can then manipulate the instrument 56 in such a way that the tip 58 engages the shallow groove 126 of the second sleeve 116 so as to introduce the tip 58 also through the recess 120 into the slot 26 of the other pedicle screw 12.

In a next step the rod 14 can be pretightened by means of the fixation screw 40 in the above-described manner. The further procedure for fixing the osteosynthesis device to the spinal column 48 corresponds to the method described above.

Figure 14:
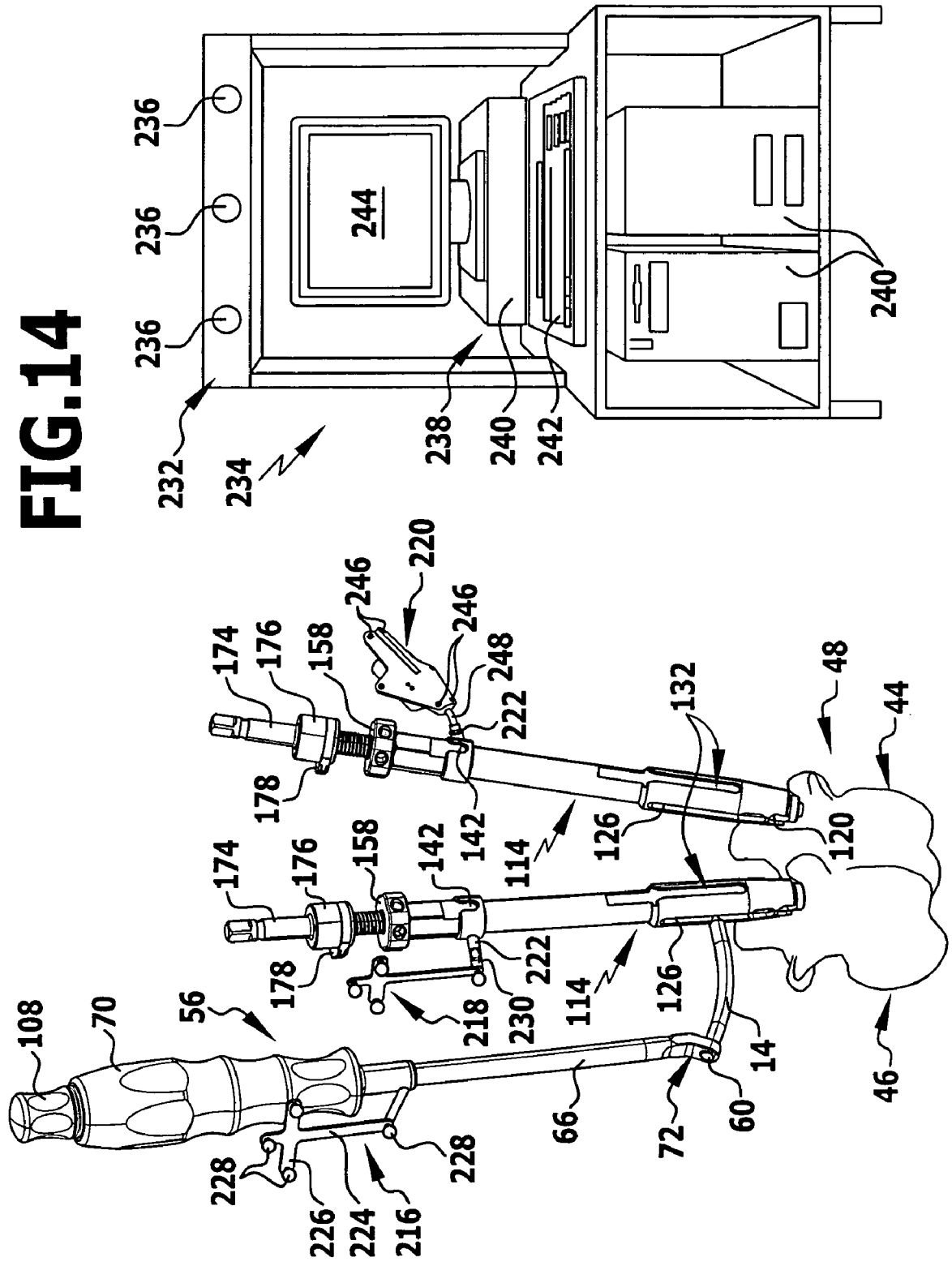
FIG. 14 is a perspective view similar to FIG. 13 with instruments provided for use in connection with a navigation system.

Optionally, both the rod insertion instrument 56 and the surgical instrument 114 can be equipped with reference elements 216, 218 and 220 which allow detection of a position and/or an orientation of the instruments 56 and 114 in a three-dimensional space defined, for example, by an operating theater. The reference elements 216, 218 and 220 can be releasably connectable to the respective instrument 56 and 114. Preferably, an adapter 222 can be provided on the instrument, for example, on the projection 140 of the instrument 114 or on the shaft 66 of the instrument 56. However, it is also possible for the reference element to be connected unreleasably to the respective instrument 56 or 114. With reference to FIG. 14, the reference element 216, for example, is unreleasably connected to the shaft 66 of the instrument 56, whereas the reference elements 218 and 220 are releasably connected by means of the adapters 222, which are provided on the respective projection 140, to the instruments 114.

The reference elements 216, 218 and 220 shown in FIG. 14 are only examples. In principle, all commonly used and available reference elements could be connected to the instrument 56 and 114. For example, reference element 216 comprises two intersecting bars 224 and 226 which carry four small spheres 228 at their free ends. The spheres 228 are provided with a surface which is well-suited for reflecting electromagnetic radiation.

The reference element 218 is of the same type as reference element 216 but comprises an adapter 230 which corresponds to the adapter 222 so that the reference element 218 can be connected to the instrument 114. The spheres 228 form marker elements which can be detected by a detection device 232 of a navigation system. The detection device 232 comprises at least one transmitter or receiver 236 which is adapted to emit and/or receive radiation, for example, electromagnetic waves or ultrasound. An alternative for a detection device would be a device which is adapted to detect modifications or changes in of an electromagnetic field induced by the reference elements. The navigation system 234 further comprises a computer system 238 for calculation of the position and/or orientation of the reference element 216, 218 and 220 in the operating theater and, therefore, determination of the position and the orientation of the instruments 56 and 114. The computer system 238 comprises at least one computer 240 with at least one commonly used input device, such as a keyboard 242, and a display 244 for displaying data processed by the computer system 238, for example, schemes or pictures indicating position and orientation of the instrument 56 and 114 in the operating theater.

The reference element 220 is a reference element of an active type which is equipped with six active marker elements 246 for emitting radiation, for example, electromagnetic waves in the infrared region or ultrasound. Furthermore, the reference element 220 has an adapter 248 which corresponds to the adapter 222 provided on the instrument 114.

Of course, the reference elements can be changed as desired, for example, if the navigation system 234 is modified from a system using electromagnetic waves as carrier to a system using ultrasound as carrier. However, the reference element could also be constructed such that disturbances or changes in an electromagnetic field established in the operating theater are detectable, which also allow detection of a position and/or an orientation of the respective reference element and, therefore, of the instrument to which the reference element is connected.

What is claimed is:

1. A surgical instrument for applying and fixing a fixation screw to an internally threaded section of a head of a bone anchorage element, the instrument comprising a distal end and a proximal end, a first tool member and a second tool member, the first tool member being arranged at the distal end and adapted for engaging the threaded section of the bone anchorage element head, and the second tool member being adapted for engaging a tool-engaging member of the fixation screw, wherein in a working position of the instrument the second tool member is supported on the instrument in a torque proof manner relative to the first tool member about a longitudinal axis and is movable parallel to the longitudinal axis relative to the first tool member, wherein the first tool member comprises a first externally threaded section corresponding to the internally threaded section of the bone anchorage element head.

2. The surgical instrument according to claim 1, wherein the first tool member is provided at a distal end of a first hollow shaft.

3. The surgical instrument according to claim 2, wherein the first hollow shaft has an internal non-circular cross section.

4. The surgical instrument according to claim 3, wherein the internal non-circular cross section is of polygonal shape.

5. The surgical instrument according to claim 1, wherein the second tool member is arranged at a distal end of a shank.

6. The surgical instrument according to claim 5, wherein the shank comprises a shaft-engaging section which has a first outer non-circular cross section.

7. The surgical instrument according to claim 6, wherein the first outer noncircular cross section is of polygonal shape.

8. The surgical instrument according to claim 6, wherein the second tool member is arranged at a distal end of the shaft-engaging section.

9. The surgical instrument according to claim 6, wherein the internal cross section of the first shaft and the external cross section of the shaft-engaging section of the shank are designed such that the shank is insertable into and movable relative to the shaft parallel to the longitudinal axis and that the shank and the shaft are supported on the instrument in a torque proof manner relative to each other.

10. The surgical instrument according to claim 1, wherein the second tool member has a second outer non-circular cross section corresponding to an internal non-circular cross section of the tool-engaging member.

11. The surgical instrument according to claim 10, wherein the second outer non-circular cross section is of polygonal shape.

12. The surgical instrument according to claim 10, wherein the first and second outer cross sections are identical.

13. The surgical instrument according to claim 5, wherein a locking mechanism is provided for locking the shaft and the shank relative to each other in at least one locking position in a direction parallel to the longitudinal axis.

14. The surgical instrument according to claim 13, wherein the locking mechanism is designed such that two locking positions are provided.

15. The surgical instrument according to claim 13, wherein in a first locking position the second tool member extends beyond a distal end of the shaft, and wherein in a second locking position the second tool member is retracted in proximal direction into the shaft.

16. The surgical instrument according to claim 13, wherein the locking mechanism comprises a first locking member and at least one second locking member, wherein in the at least one locking position the first locking member engages the at least one second locking member, and wherein in a release position the first locking member disengages from the at least one second locking member.

17. The surgical instrument according to claim 16, wherein the first locking member is movably supported on the shank, and wherein the at least one second locking member is arranged on the shaft.

18. The surgical instrument according to claim 16, wherein the at least one second locking member is designed in the form of a locking recess.

19. The surgical instrument according to claim 18, wherein the locking recess is designed in the form of a peripheral groove.

20. The surgical instrument according to claim 13, wherein a first stop is provided for defining and separating first and second axial locking positions.

21. The surgical instrument according to claim 20, wherein the stop is designed in the form of a peripheral projection axially separating two second locking members.

22. The surgical instrument according to claim 16, wherein the first locking member is biased into engagement with the at least one second locking member.

23. The surgical instrument according to claim 22, wherein a bias member is provided for biasing the first locking member into engagement with the at least one second locking member.

24. The surgical instrument according to claim 23, wherein the bias member is a spring.

25. The surgical instrument according to claim 13, wherein a proximal end of the shank extends beyond a proximal end of the shaft in the at least one locking position.

26. The surgical instrument according to claim 1, wherein a handle is provided at the proximal end of the instrument.

27. The surgical instrument according to claim 26, wherein the handle is releasably connectable to the instrument.

28. The surgical instrument according to claim 27, wherein the handle is releasably connectable to the proximal end of the shank.

29. The surgical instrument according to claim 1, wherein the instrument further comprises a tubular outer sleeve which is engageable with the bone anchorage element and which is configured to receive the first and second tool members.

30. The surgical instrument according to claim 29, wherein the sleeve is dimensioned such that the first hollow shaft is insertable into and extractable out of the sleeve in a direction parallel to a longitudinal axis defined by the sleeve.

31. A surgical instrument for applying and fixing a fixation screw to a threaded section of a head of a bone anchorage element, the instrument comprising a distal end and a proximal end, a first tool member and a second tool member, the first tool member being arranged at the distal end and adapted for engaging the threaded section of the bone anchorage element head, and the second tool member being adapted for engaging a tool-engaging member of the fixation screw, wherein in a working position of the instrument the second tool member is supported on the instrument in a torque proof manner relative to the first tool member about a longitudinal axis and is movable parallel to the longitudinal axis relative to the first tool member, wherein the instrument further comprises at least one distractor-engaging portion for connecting the instrument to a distractor.

32. The surgical instrument according to claim 31, wherein the at least one distractor-engaging portion is designed in the form of a receiver.

33. The surgical instrument according to claim 32, wherein the receiver is designed in the form of a groove.

34. The surgical instrument according to claim 33, wherein the groove is undercut.

35. The surgical instrument according to claim 33, wherein the groove has an internal cross section in the form of a T.

36. The surgical instrument according to claim 31, wherein a first distractor-engaging portion is provided on a distal end portion of the sleeve, and a second distractor-engaging portion is provided on a proximal end portion of the sleeve.

37. The surgical instrument according to claim 31, wherein the at least one distractor-engaging portion comprises an insertion opening which is open in proximal direction.

38. The surgical instrument according to claim 29, wherein the sleeve comprises at least one first guide member for cooperating with a corresponding second guide member provided on the bone anchorage element head in such a way that the sleeve is engageable with the bone anchorage element in at least one selected position.

39. The surgical instrument according to claim 38, wherein the sleeve is provided with an insertion recess at a distal end, the insertion recess being alignable with a connection member receiver of the bone anchorage element head by means of the at least one first and second guide members such that a connection member is insertable through the recess into the connection member receiver.

40. The surgical instrument according to claim 38, wherein the at least one first guide member partially engages the connection member receiver in the at least one selected position.

41. The surgical instrument according to claim 38, wherein the sleeve comprises two first guide members arranged in diametrically opposed relation to a longitudinal axis of the sleeve.

42. The surgical instrument according to claim 39, wherein the sleeve comprises a connection member guide for guiding a connection member or a portion thereof into the insertion recess.

43. The surgical instrument according to claim 42, wherein the connection member guide comprises a shallow guiding recess extending from the insertion recess in proximal direction.

44. The surgical instrument according to claim 29, wherein a proximal end or a proximal end portion of the sleeve is provided with a polygonal external cross section.

45. The surgical instrument according to claim 29, wherein a clamping mechanism is provided for keeping the sleeve in a clamped relation with the bone anchorage element in a clamping position.

46. The surgical instrument according to claim 45, wherein the clamping mechanism comprises a clamping member supported on the shaft for clamping the sleeve between the bone anchorage element and the clamping member in the clamping position.

47. The surgical instrument according to claim 46, wherein the shaft comprises a second externally threaded section at its proximal end, and the clamping member is designed in the form of a counter nut which is threadingly engageable with the second externally threaded section of the shaft.

48. The surgical instrument according to claim 1, wherein a thread pitch of threads of the first externally threaded section is equal to or larger than a thread pitch of threads of the fixation screw.

49. A surgical instrument for applying and fixing a fixation screw to a threaded section of a head of a bone anchorage element, the instrument comprising a distal end and a proximal end, a first tool member and a second tool member, the first tool member being arranged at the distal end and adapted for engaging the threaded section of the bone anchorage element head, and the second tool member being adapted for engaging a tool-engaging member of the fixation screw, wherein in a working position of the instrument the second tool member is supported on the instrument in a torque proof manner relative to the first tool member about a longitudinal axis and is movable parallel to the longitudinal axis relative to the first tool member, wherein a reference element is provided on the instrument, the reference element being constructed such that it is detectable by a detection device of a navigation system.

50. The surgical instrument according to claim 49, wherein the reference element is releasably connectable to the instrument.

* * * * *